(12) United States Patent
Marshall et al.

(10) Patent No.: US 8,404,838 B2
(45) Date of Patent: Mar. 26, 2013

(54) INHIBITORS OF TYROSINE KINASE RECEPTOR DIMERIZATION

(75) Inventors: Garland R. Marshall, Clayton, MO (US); Linda J. Pike, Clayton, MO (US); Robert Yang, Medford, MA (US)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 13/157,472

(22) Filed: Jun. 10, 2011

(65) Prior Publication Data

US 2011/0312919 A1    Dec. 22, 2011

Related U.S. Application Data

(62) Division of application No. 12/384,511, filed on Apr. 6, 2009, now abandoned.

(60) Provisional application No. 61/042,715, filed on Apr. 5, 2008.

(51) Int. Cl.
*C07D 473/00*    (2006.01)

(52) U.S. Cl. ..................................................... 544/264

(58) Field of Classification Search .................. 544/264
See application file for complete search history.

(56) References Cited

PUBLICATIONS

Brooks, et al. Journal of Chemical Information and Modeling, 47(5), 2007, 1897-1905.*

* cited by examiner

*Primary Examiner* — Douglas M Willis
(74) *Attorney, Agent, or Firm* — Zackson Law LLC; Saul L. Zackson

(57) ABSTRACT

The teachings relate to methods of identifying inhibitors of dimerization of tyrosine receptor kinases such as EGFR. The methods comprise providing, on a digital computer, a molecular model comprising a complex of extracellular dimerization domains of an RTK, docking a chemical databases to the molecular model, scoring the compounds comprised by the database, and identifying one or more high-scoring compounds. The methods further comprise testing a compound for RTK inhibitory activity in vitro, and testing a compound for specificity as an RTK inhibitor. Also disclosed are compounds selected by the described methods, and methods of treatment using the compounds. Two compounds (NSC11241 and NSC56452) are disclosed that inhibit EGF receptor kinase activation in a dose-dependent manner.

5 Claims, 12 Drawing Sheets

INHIBITORS OF TYROSINE KINASE RECEPTOR DIMERIZATION

CROSS-REFERENCE TO RELATED APPLICATIONS

The present application is a division of U.S. patent application Ser. No. 12/384,511, filed Mar. 6, 2009, which claims priority to U.S. Provisional Application Ser. No. 61/042,715, filed Apr. 5, 2008. These applications are hereby incorporated by reference, each in its entirety.

STATEMENT REGARDING FEDERALLY SPONSORED RESEARCH OR DEVELOPMENT

The disclosed subject matter was developed in part with Government support under U.S.P.H.S. Grants RO1-68460 and RO1-064491 awarded by the National Institutes of Health. The Government has certain rights in the invention.

BACKGROUND

1. Field

The disclosed subject matter relates to inhibitors of tyrosine kinase receptors (RTKs) such as EGFR, and methods of screening for compounds which inhibit RTK activity. In particular, the disclosed subject matter relates in inhibitors of RTK dimerization including EGFR dimerization, and methods of screening for such inhibitors.

2. Introduction

Protein kinases (PKs) are enzymes that catalyze the phosphorylation of hydroxy groups on tyrosine, serine and threonine residues of proteins. The consequences of this seemingly simple action are profound; cell growth, differentiation and proliferation; i.e., virtually all aspects of cell life, in one way or another, depend on PK activity. Abnormal PK activity has been related to a host of disorders, ranging from relatively non life-threatening diseases such as psoriasis to extremely virulent diseases such as glioblastoma (brain cancer).

Certain growth factor receptors exhibiting PK activity are known as receptor tyrosine kinases (RTKs). RTKs comprise a large family of transmembrane receptors with diverse biological activity. As present, at least nineteen (19) distinct subfamilies of RTKs have been identified. One RTK subfamily contains the insulin receptor (IR), insulin-like growth factor I receptor (IGF-IR) and insulin receptor related receptor (IRR). IR and IGF-IR interact with insulin to activate a hetero-tetramer composed of two entirely extracellular glycosylated alpha subunits and two beta subunits which cross the cell membrane and which contain the intracellular tyrosine kinase domain. The Insulin-like Growth Factor-1 Receptor (IGF-1R), and its ligands, IGF-1 and IGF-2, are abnormally expressed in numerous tumors, including, but not limited to, breast, prostate, thyroid, lung, hepatoma, colon, brain and neuroendocrine. A more complete listing of the known RTK subfamilies is described in Plowman et al., KN&P, 1994, 7(6):334-339 which is incorporated by reference in its entirety herein.

RTKs have been implicated in a host of pathogenic conditions including cancer. Other pathogenic conditions, which have been associated with abnormal RTK activity include, without limitation, psoriasis, hepatic cirrhosis, diabetes, atherosclerosis, angiogenesis, restenosis, ocular diseases, rheumatoid arthritis and other inflammatory disorders, autoimmune diseases and a variety of renal disorders.

The epidermal growth factor receptor (EGFR) is a prototypical RTK. The EGF receptor stimulates a complex signaling cascade that ultimately promotes cell proliferation, survival, and migration (Yarden, Y. & Schlessinger, J., Biochemistry 26, 1443-1451, 1987). Not surprisingly, perturbation of the EGF receptor system leads to a variety of tumors in organs including breast, brain, lung, ovary, and prostate (Normanno, N., et al., Gene 366, 2-16, 2006). In particular, 70-80% of metaplastic breast carcinomas over-express the EGF receptor (Reis-Filho, J., et al., Breast Cancer Research 7, R1028-R1035; http://breast-cancer-research.com/content/7/6/R10282005), and 40-80% of non-small cell lung cancers arise from EGF receptor over-expression and/or mutation (Grandis, J. R. & Sok, J. C., Pharmacol. Ther. 102, 37-46, 2004).

As a validated target in oncology, EGFR has been extensively studied and its intracellular signaling pathways mapped as described in Oda et al. Mol Systems Biol, 2005, 1(1): 1-17 which is incorporated by reference in its entirety herein. EGFR and ErbB2 belong to the ErbB family of receptor tyrosine kinases (RTK). They are characterized by an extracellular ligand-binding domain, a single transmembrane helix, an intracellular kinase domain, and a C-terminal tail (FIG. 1A). The receptors are thought to exist predominantly as monomers in the plasma membrane. Upon binding of ligands to the extracellular domain, EGF and ErbB receptors homo- or heterodimerize with each other (FIG. 1B). Receptor dimerization leads to kinase activation, resulting in transphosphorylation of specific tyrosine residues within the C-terminal tail of the extracellular domain of the receptor which facilitate dimerization. In particular, single mutation to either Y246 or Y251, two strictly conserved tyrosines on the "arm", is enough to completely abolish dimerization (Dawson, J. P., et al., Mol. Cell. Biol. 25, 7734-7742, 2005; Walker, F., et al., J. Biol. Chem. 279, 22387-22398, 2004).

ErbB receptor dimerization is a pre-requisite for receptor activation and is driven by interactions between the extracellular domains (ECD) of the two partners. In the inactive monomeric state, the EGFR ECD adopts a tethered conformation where a long loop from domain II, known as the dimerization arm, is held between domain II and domain IV. Binding of growth factors like EGF to the ECD induces a large conformational arrangement (FIG. 2) where the dimerization arm is exposed to the environment in a conformation known as the extended conformation.

EGFR or ECDs thereof have been crystallized either with or without a ligand bound, and three-dimensional structures, including atomic coordinates, have been reported. (Ogino, H., et al., Cell 110, 775-787, 2002; Cho, H.-S., et al., Science 297, 1330-1333, 2002; Garrett, T. P. J. et al., Cell 110, 763-773, 2002). Atomic coordinates are available on the internet at http://www.rcsb.org/pdb/home/home.do (Berman, H. M., et al., Nucleic Acids Research 28, 235-242, 2000). The crystal structures show that the aromatic rings of Y246 and Y251 on one monomer pack nicely into a pair of adjacent "pockets" on the other monomer (FIG. 1). The crystal structures of the EGFR extracellular domain homodimer show that the most extensive part of the dimer interface is centered on the intermolecular interaction between the dimerization arms of two monomers. The dimerization arm (residues 242-259) buries more than 800 Å2 of surface area and is specific to the ErbB family receptors. EGFR with mutations on the dimerization arm fail to form dimers confirming the critical role of the "arm" in dimerization. In particular, single mutation to either Y246 or Y251, two strictly conserved tyrosines on the "arm", is enough to completely abolish dimerization. The crystal structure shows that the aromatic rings of Y246 and Y251 on one monomer pack nicely into a pair of adjacent "pockets" on the other monomer (FIG. 2-3). In addition to the van der Waal interactions, the hydroxyl group of Y246 forms hydrogen bonds with G264 and C283, and has been suggested to be critical since dimerization is abolished in a Y246F mutant.

Given its strong association with cancer, the EGF receptor is a validated target in the emerging paradigm of mechanism-based cancer therapeutics (Ciardiello, F. Future Oncology 1, 221-234, 2005; Hynes, N. E. & Lane, H. A., Nat. Rev. Cancer 5, 341-354, 2005; Marshall, J., Cancer 107, 1207-1218, 2006). Current EGF receptor-directed strategies include monoclonal antibodies that target the extracellular domain (Kirkpatrick, P., et al., Nat. Rev. Drug Discov., 3, 549-550, 2004; Saltz, L., et al., Nat. Rev. Drug Discov. 5, 987-988, 2006), and small-molecule tyrosine kinase inhibitors that compete with ATP at the nucleotide binding site of the kinase domain (Dowell, J., et al., Nat. Rev. Drug Discov. 4, 13-14, 2005; Moy, B., et al., Nat. Rev. Drug Discov. 6, 431-432, 2007; Muhsin, M., et al., Nat. Rev. Drug Discov. 2, 515-516, 2003). These drugs have utility, but show highly variable efficacy in clinical applications (Pao, W., et al., PLoS Medicine 2, e73 2005; Perez-Soler, R., et al., Oncologist 9, 58-67, 2004). Recent reports showed that some of the clinical variability is due to an increasing number of cases where tumors develop resistance to the tyrosine kinase inhibitors by mutation of residues within the ATP binding site of the kinase domain (Bell, D. W., et al., Nat. Genet. 37, 1315-1316, 2005; Sharma, S. V., et al., Nat. Rev. Cancer 7, 169-181, 2007).

SUMMARY

The above findings suggested to the inventors that dimer stabilization requires the proper interaction between Y246/Y251 and the corresponding binding "pockets" that can be sensitive to even a small perturbation. The present inventors have realized that this sensitivity to perturbation presents an exciting opportunity for the application of structural-based lead discovery of novel inhibitors that can disrupt the Y246/Y251 interface. In view of the need for new reagents for diagnosis, prevention or treatment of diseases which involve RTKs such as EGFR, the present inventors have realized that the extracellular region of EGFR is a good target for a drug which decreases activity of RTKs such as EGFR. The present inventors have thus developed methods of screening for compounds that inhibit RTK activity, in particular for compounds which interfere with dimerization of the extracellular domain (ECD), and have used these methods to identify novel inhibitors.

In various embodiments, the methods developed by the present inventors, can involve multilevel investigations, such as analysis of three-dimensional structures and models of EGFR-ligand complexes, and various analytical tools, including virtual docking of chemical databases to RTK dimerization domains and in silico high throughput screening of chemical structures as potential inhibitors; tests of candidate compounds for inhibitory effects on EGFR activity, tests for specificity of candidate compounds, and/or tests to investigate the effects of a candidate inhibitor on dimerization. In other aspects, the present inventors provide examples of compounds which inhibit EGFR activity and were identified using these methods. These compounds include lead compounds comprising a core structure, and derivatives thereof which comprise the same core structure.

In some aspects, methods of the present teachings can include identifying the binding site for a beta-hairpin loop involved in hetero- or homo-dimerization, in a computer-based model of an RTK such as EGFR or an ECD dimer thereof. To identify candidate inhibitors, this site can be targeted by docking and scoring of compounds comprised by one or more libraries of virtual compounds. High scoring candidate compounds can be purchased and/or synthesized. A candidate compound can then be tested for (i) its ability to inhibit signal transduction by an RTK such as EGFR, which can include the compound's ability to inhibit tyrosine kinase activity of the RTK; (ii) its specificity against an RTK (such as EGFR) compared to other RTKs; and (iii) its ability to inhibit chemical cross-linking of an RTK ECD when the RTK is stimulated with a natural ligand (e.g., an EGFR stimulated with epidermal growth factor).

In some aspects, the present inventors have developed methods for designing a drug which inhibits activity of an EGFR. In various configurations, these methods comprise providing on a digital computer a three-dimensional structure of an EGFR ECD-ligand complex comprising the EGFR ECD dimer and an EGFR ligand; using software comprised by the digital computer to design a chemical compound which is predicted to bind to an EGFR ECD dimer, and in particular to the interface between domains comprising ECDs in a dimer. In some aspects, the methods can involve virtual screening not only of an actual 3-dimensional structure of an EGFR dimer developed using x-ray crystallography, but also virtual screening of a homology model, whereby candidate inhibitory compounds are identified using conceptual structures of homodimerized and/or heterodimerized extracellular domains of an RTK such as EGFR.

Also disclosed herein are methods for testing a compound as an RTK inhibitor in a cell or tissue. These methods comprise: selecting a candidate inhibitor of EGFR activity by performing a structure-based drug design using a three-dimensional structure determined for a crystal comprising an EGFR ECD; contacting the cell or tissue with the candidate inhibitor; and determining a change of an activity of an RTK comprised by the cell or tissue.

In yet other aspects, the present teachings include methods for decreasing an RTK activity such as EGFR activity in a subject for the treatment of a disease. These methods can comprise selecting a compound identified as an inhibitor of EGFR dimerization using a three-dimensional structure determined for a crystal comprising an EGFR ECD, and administering a therapeutically effective amount of the inhibitor to a subject in need thereof. A disease of these aspects can be, without limitation, a cancer such as a cancer of the breast, a cancer of the ovary or the uterus.

In yet other aspects, the present teachings include compounds identified by the screening methods set forth herein, as well as salts thereof such as pharmaceutically acceptable salts. In some configurations, the present teachings include stereoisomers of the compounds, and salts thereof. The compounds can function as inhibitors of RTK dimerization, in particular of EGFR dimerization, and can be used in therapeutic applications such as oncology (such as, for example, breast, ovarian, or uterine cances) and/or in a research context.

In some aspects, a screening method of the present teachings includes the following "top-down" approach to identifying lead compounds which inhibit dimerization of RTKs such as EGFR, including the following levels of analysis (FIG. 4; FIG. 5):

First, on level 1, putatitive candidate compounds are selected. Selection of these compounds comprises virtual docking of a chemical database to an RTK dimerization "hot-spot." Level 2 comprises testing the candidate compounds for activity as inhibitors of RTK activation, such as, for example, EGFR activation. These methods can comprise assays for RTK activity that are well known to skilled artisans, such as, for example, Western blot assays on RTK autophosphorylation. In level 3, compounds can be tested for selectivity using methods well known to skilled artisans, such as, for example, Western blot assays for effects of a compound on related RTKs and G-protein coupled receptors. In level 4, further analysis of a candidate compound can comprise investigations into mechanism, such as, in non-limiting example, split-luciferase assays, cross-linking assays, and RTK binding assays. In level 5, lead candidate compounds can be optimized. This optimization can comprise performing a structural similarity search for related compounds in at least one additonal database, which can be, for example a larger database. The optimization level analysis can also comprise synthesis of a focused combichem library. Because the last level can suggest new compounds to test, in some configurations, these new compounds can be taken through the levels in a new cycle of analysis.

In some aspects, the present teachings include lead compounds identified by the present methods, such as the compounds disclosed in Table 1, as well as salts thereof, including pharmaceutical salts, as well as various isomers, analogues and salts thereof. The present teaching thus include the following compounds and salts thereof.

TABLE 1

Lead compounds that inhibit EGFR dimerization, discovered by the disclosed methods.

| Inhibitor No. | IC50 (μM) | Dimer inhibition |
|---|---|---|
| NSC11241 | 12.8 | ++ |
| NSC309895 | 24.4 | + |
| NSC303769 | 3.97 | + |
| NSC56452 | 0.39 | + |

The structures of these compounds are as follows:

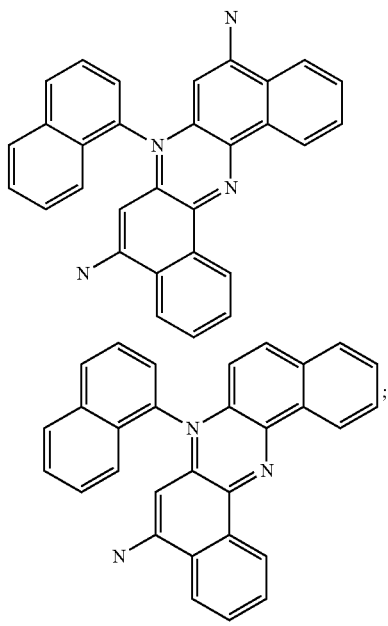

NSC11241

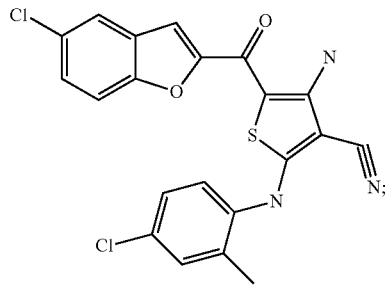

NSC309895

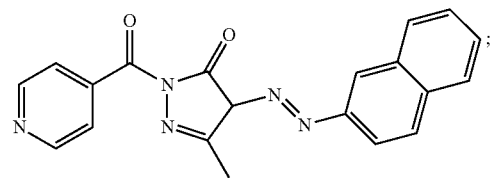

NSC303769

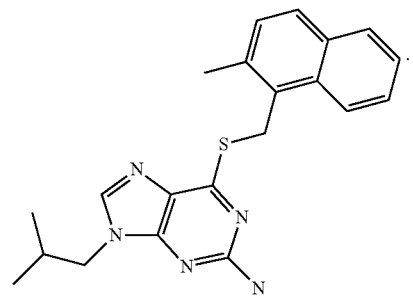

NSC56452

A. Compound NSC11241 and its analogs include:

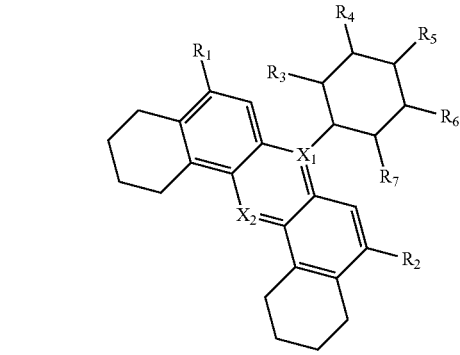

wherein 5- or 6-membered rings are either aromatic or aliphatic; $X_1$ is C, N, or S; $X_2$ is C, N or S; $R_1$ is H, alkyl, cycloalkyl, alkenyl, alkynyl, halo, heteroaryl or heterocycle; $R_2$ is H, alkyl, cycloalkyl, alkenyl, alkynyl, halo, heteroaryl or heterocycle; $R_3$ is H, alkyl, cycloalkyl, alkenyl, alkynyl, halo, heteroaryl or heterocycle; $R_4$ is H, alkyl, cycloalkyl, alkenyl, alkynyl, halo, heteroaryl or heterocycle; $R_5$ is H, alkyl, cycloalkyl, alkenyl, alkynyl, halo, heteroaryl or heterocycle; $R_6$ is H, alkyl, cycloalkyl, alkenyl, alkynyl, halo, heteroaryl or heterocycle; $R_7$ is H, alkyl, cycloalkyl, alkenyl, alkynyl, halo, heteroaryl or heterocycle.

B. Compound NSC309895 and its analogs include:

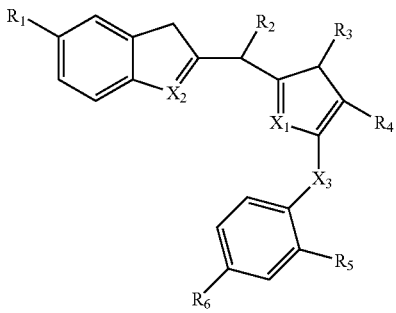

wherein 5- or 6-membered rings are either aromatic or aliphatic; $X_1$ is C, O, N, or S; $X_2$ is C, O, N, or S; $X_3$ is C, O, N, or S; and $R_1$ is H, alkyl, cycloalkyl, alkenyl, alkynyl, halo, heteroaryl or heterocycle; $R_2$ is H, alkyl, cycloalkyl, alkenyl, alkynyl, halo, heteroaryl or heterocycle; $R_3$ is H, alkyl, cycloalkyl, alkenyl, alkynyl, halo, heteroaryl or heterocycle; $R_4$ is H, alkyl, cycloalkyl, alkenyl, alkynyl, halo, heteroaryl or heterocycle; $R_5$ is H, alkyl, cycloalkyl, alkenyl, alkynyl, halo, heteroaryl or heterocycle; $R_6$ is H, alkyl, cycloalkyl, alkenyl, alkynyl, halo, heteroaryl or heterocycle.

C. Compound NSC303769 and its analogs include:

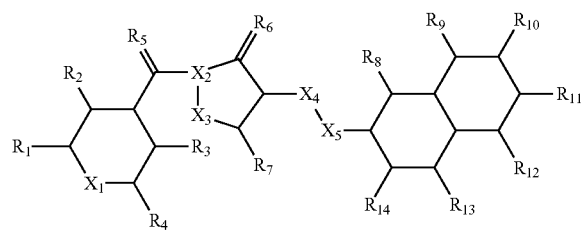

wherein 5- or 6-membered rings are either aromatic or aliphatic; $X_1$ is C, O, N or S; $X_2$ is C, O, N or S; $X_3$ is C, O, N or S; $X_4$ is C, O, N or S; $X_5$ is C, O, N or S; and $R_1$ is H, alkyl, cycloalkyl, alkenyl, alkynyl, halo, heteroary or heterocycle; $R_2$ is H, alkyl, cycloalkyl, alkenyl, alkynyl, halo, heteroary or heterocycle; $R_3$ is H, alkyl, cycloalkyl, alkenyl, alkynyl, halo, heteroary or heterocycle; $R_4$ is H, alkyl, cycloalkyl, alkenyl, alkynyl, halo, heteroary or heterocycle; $R_5$ is C, N, O, S; $R_6$ is C, N, O, S; $R_7$ is H, alkyl, cycloalkyl, alkenyl, alkynyl, halo, heteroary or heterocycle;

$R_8$ is H, alkyl, cycloalkyl, alkenyl, alkynyl, halo, heteroary or heterocycle; $R_9$ is H, alkyl, cycloalkyl, alkenyl, alkynyl, halo, heteroary or heterocycle; $R_{10}$ is H, alkyl, cycloalkyl, alkenyl, alkynyl, halo, heteroary or heterocycle; $R_{11}$ is H, alkyl, cycloalkyl, alkenyl, alkynyl, halo, heteroary or heterocycle; $R_{12}$ is H, alkyl, cycloalkyl, alkenyl, alkynyl, halo, heteroary or heterocycle; $R_{13}$ is H, alkyl, cycloalkyl, alkenyl, alkynyl, halo, heteroary or heterocycle; $R_{13}$ is H, alkyl, cycloalkyl, alkenyl, alkynyl, halo, heteroary or heterocycle.

D. Compound NSC56452 and its analogs include:

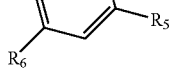

wherein 5-(ring D) or 6-membered rings (A, B or C) are either aromatic or aliphatic; $X_1$ is C, O, N or S; $X_2$ is C, O, N or S; $X_3$ is C, O, N or S; $X_4$ is C, O, N or S; $X_3$ is C, O, N or S; and $R_1$ is H, alkyl, cycloalkyl, alkenyl, alkynyl, halo, heteroary or heterocycle; $R_2$ is H, alkyl, cycloalkyl, alkenyl, alkynyl, halo, heteroary or heterocycle; $R_3$ is H, alkyl, cycloalkyl, alkenyl, alkynyl, halo, heteroary or heterocycle; $R_4$ is H, alkyl, cycloalkyl, alkenyl, alkynyl, halo, heteroary or heterocycle; $R_5$ is H, alkyl, cycloalkyl, alkenyl, alkynyl, halo, heteroary or heterocycle; $R_6$ is H, alkyl, cycloalkyl, alkenyl, alkynyl, halo, heteroary or heterocycle; $R_7$ is H, alkyl, cycloalkyl, alkenyl, alkynyl, halo, heteroary or heterocycle; $R_8$ is H, alkyl, cycloalkyl, alkenyl, alkynyl, halo, heteroary or heterocycle; $R_9$ is H, alkyl, cycloalkyl, alkenyl, alkynyl, halo, heteroary or heterocycle.

In some aspects of the present teachings, the inventors disclose methods of inhibiting growth of cancer cells. The inhibition can be in vitro, or in vivo, e.g., in the treatment of a cancer. In various configurations, these methods comprise contacting cancer cells with an inhibitor described herein, such as NSC11241, NSC309895, NSC303769, NSC56452, or a salt thereof. In some aspects, these methods can further comprise contacting the cancer cells with at least one second inhibitor, such as, without limitation, an EGF Receptor tyrosine kinase inhibitor that is known to skilled artisans (see, e.g., Dowell, J., et al., Nat. Rev. Drug Discov. 4, 13-14, 2005; Moy, B., et al., Nat. Rev. Drug Discov. 6, 431-432, 2007; Muhsin, M., et al., Nat. Rev. Drug Discov. 2, 515-516, 2003; Ciardiello, F., et al., Clin. Cancer Res. 7, 2958-2970, 2001; Stamos, J., et al., J. Biol. Chem. 277, 46465-46272, 2002). Without limitation, examples of such kinase inhibitors include AG1478, and erlotinib (Akita, R. W., et al., Semin. Oncol. 30 (3 Suppl 7), 15-24, 2003; Hidalgo, M., et al., Semin. Oncol. 30 (3 Suppl 7), 25-33, 2003; Herbst, R. S., Semin. Oncol. 30 (3 Suppl 7), 34-46, 2003; Bulgaru, A. M., et al., Expert Rev. Anticancer Ther. 3, 269-279, 2003).

These and other features, aspects and advantages of the present teachings will become better understood with reference to the following description, examples, and appended claims.

DETAILED DESCRIPTION

Systematic screening of diverse compound libraries using high-throughput facilities has emerged as an important strategy for the discovery of inhibitors of protein-protein interactions. Unfortunately, in addition to the high cost of library preparation, high-throughput screening is not always feasible due to the lack of appropriate high-throughput bioassays. In this work, the present inventors utilized virtual high-throughput screening in combination with low-throughput biochemical assays to screen for novel compounds that inhibit the EGF receptor in intact cells. NSC11241 and NSC56452 were identified as small molecule inhibitors of EGF receptor dimerization and activation.

Figure 1:
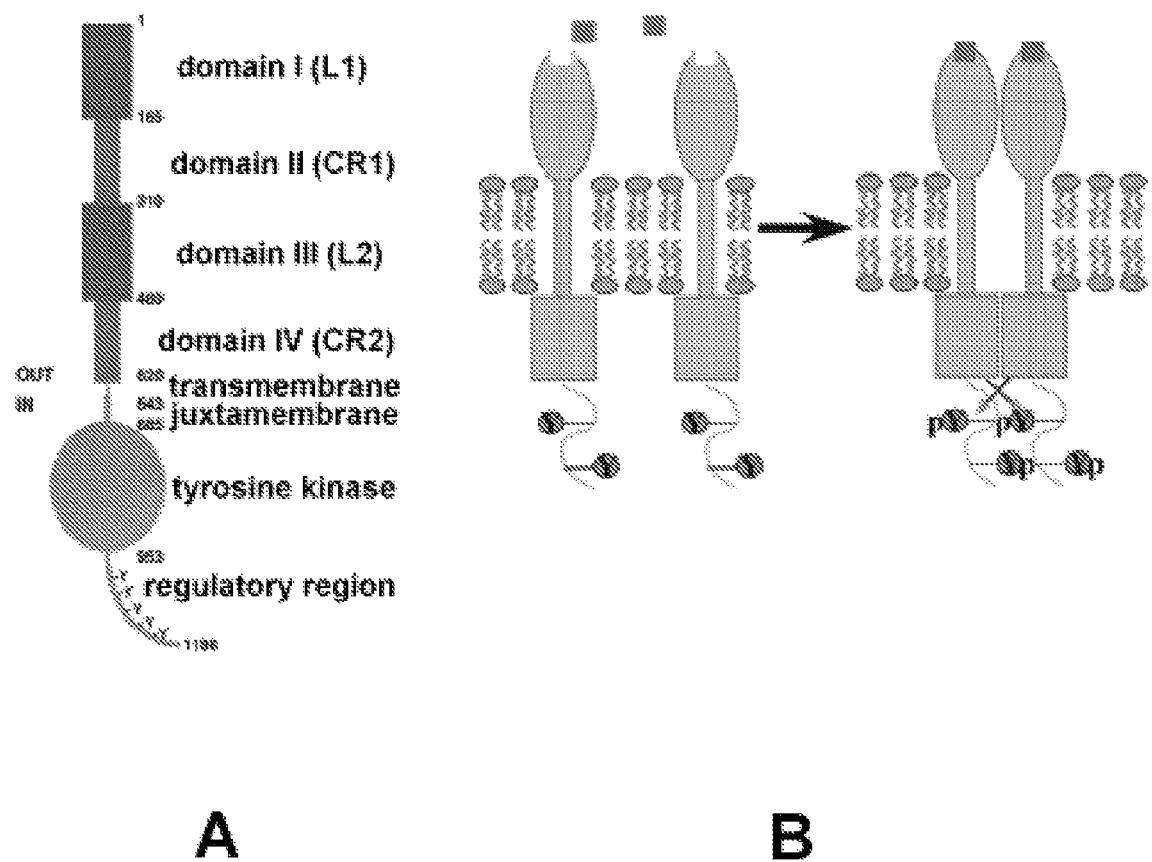
FIG. 1 illustrates structure of the ErbB family of receptors. A) Schematics of ErbB family, adapted from Burgess et al., Mol. Cell. 12: 541-552, 2003. B) tyrosines in dimerization anus serve a docking critical role of the "arm". Dimerization of the extracellular domains forces proximity of intracellular tyrosine kinase domains that undergo autophosphorylation and subsequent signal transduction.
Figure 2:
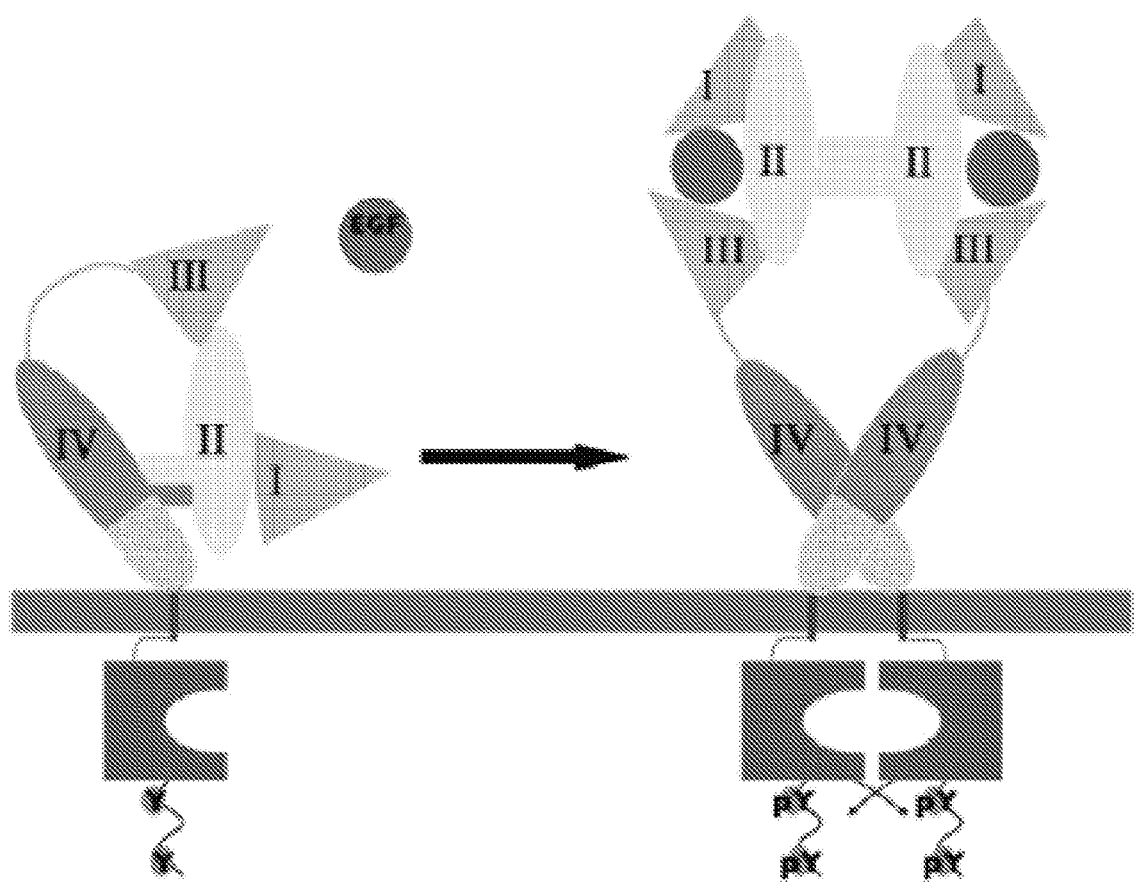
FIG. 2 illustrates a schematic representation of the EGFR extracellular domain (ECD) dimer. In the absence of ligands, EGFR monomer is held in a tethered conformation through contacts between subdomains II and IV. Ligand binding induces a dramatic conformational change that disrupts the intramolecular tether and extends the dimerization arm in subdomain 11E.
Figure 3:
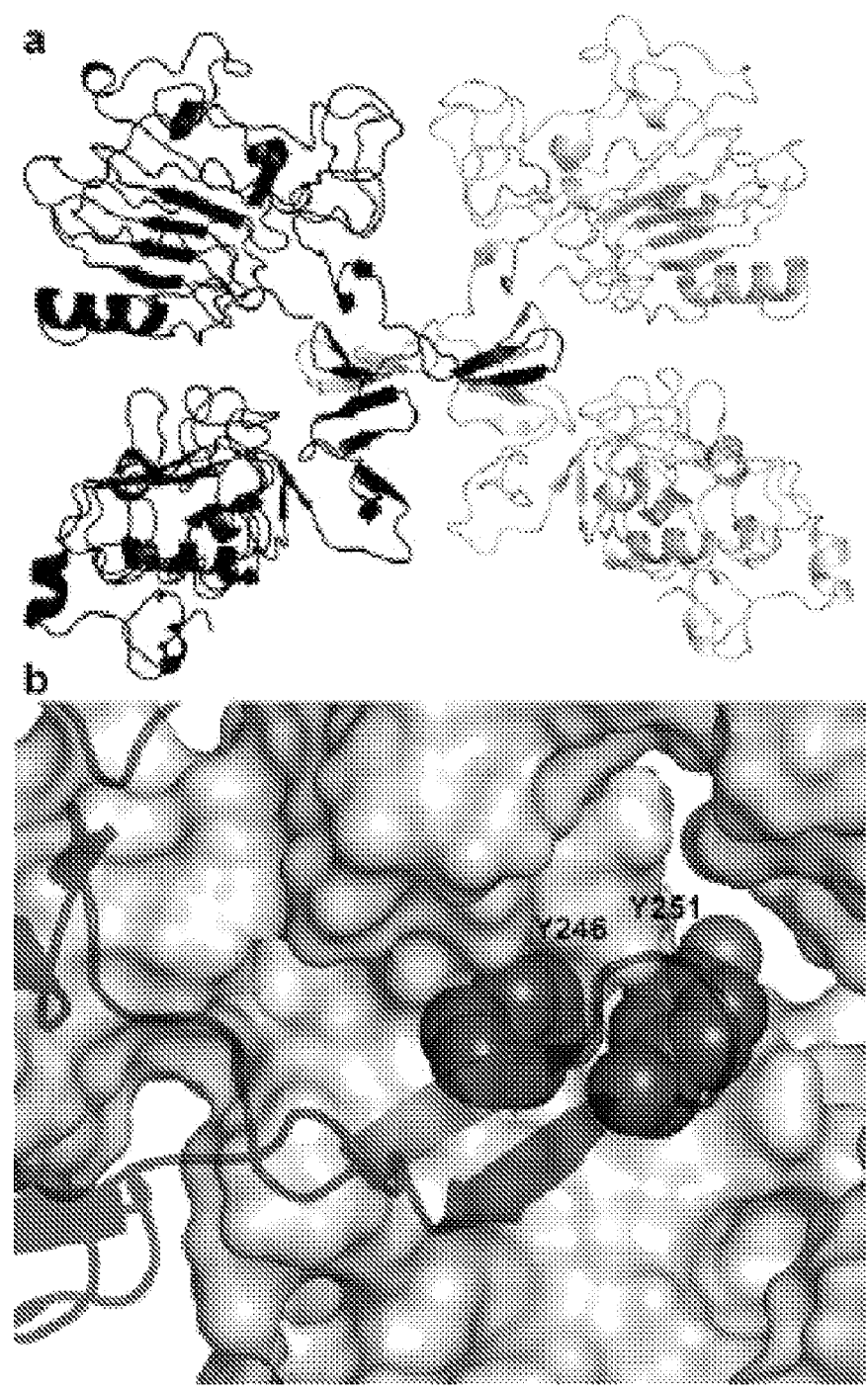
FIG. 3 illustrates the target site of the EGFR dimerization interface. A) Extracellular domain of EGFR homodimer (PDB:1MOX) and the dimerization arm (box). B) Critical residues Y246 and Y251 pack to adjacent pockets at the dimer interface.

In identifying these inhibitors, we took advantage of the recent finding that the B-hairpin loop extending from the back of subdomain II of the extracellular domain of the EGF receptor plays an important role in mediating EGF receptor dimerization (Dawson, J. P., et al., Future Oncology 1, 221-234, 2005; Ferguson, K. M., et al., EMBO J. 19, 4632-4643, 2000; Garrett, T. P. J., et al., Cell 110, 763-773, 2002; Ogiso, H., et al., Cell 110, 775-787, 2002; Walker, F., et al., J. Biol. Chem. 279, 22387-22398, 2004). Structural and mutational data have demonstrated that the aromatic rings of Tyr246/Tyr-25 1 from the dimerization arm of one monomer pack tightly into a pair of adjacent pockets on the other monomer. This interaction occurs in a precise orientation, and is intolerant to minor perturbations (FIG. 3). For example, mutations such as Y246F (Dawson, J. P., et al., Mol. Cell. Biol. 25, 7734-7742, 2005), and Y251F/R285A (Walker, F., et al., J. Biol. Chem. 279, 22387-22398, 2004) are sufficient to completely abolish dimerization. This demonstrates the critical and sensitive interactions between the two tyrosine side chains and their binding pockets. We hypothesized that this sensitivity could be exploited to discover compounds capable of interfering with the protein-protein interactions necessary for EGF receptor dimerization.

By testing only 4% of the NCI compound library, NSC11241 and NSC56452 were identified as compounds that specifically inhibited EGF-stimulated kinase activity. They were not effective against the related PDGF and insulin receptor tyrosine kinases. Several lines of evidence suggest that NSC11241 and NSC56452 work by inhibiting the dimerization of the EGF receptor. First, the compounds had very little effect on the binding of EGF. Second, the compounds inhibited EGF-induced crosslinking of the receptor into high molecular weight oligomers. Finally, the compounds inhibited luciferase activity in a luciferase fragment complementation assay designed for monitoring the dimerization of the extracellular domain of the EGF receptor (Yang, K. S., et al., J. Biol. Chem. 284, 7474-7482, 2009). Taken together, these data suggest that NSC11241 and NSC56452 inhibit EGF receptor function via a novel mode of action-inhibition of dimer formation.

These compounds serve as a proof-of-principle for identifying a new class of small-molecule drug-like inhibitors, whose target site and mechanism differ from those of the traditional small-molecule tyrosine kinase inhibitors. Inhibitors identified by the inventors as by the present methods blocked EGF receptor dimer formation as measured by both chemical crosslinking and luciferase fragment complementation while AG1478, an EGF receptor-specific tyrosine kinase inhibitor, increased dimer-formation as measured by both assays (Gan et al., J. Biol. Chem. 282, 2840-2850, 2007;

Yang, K. S., et al., J. Biol. Chem. 284, 7474-7482, 2009). These results underscore the difference in mechanism between small-molecule tyrosine kinase inhibitors and our inhibitors of dimerization. Consistent with their different mechanisms, NSC56452 and the tyrosine kinase inhibitor, erlotinib, were additive with respect to their ability to inhibit cancer cell growth.

As drug-like molecules that target the extracellular domain, this new class of EGF receptor inhibitors can bypass several current problems associated with clinical efficacy. In contrast to large biologics, small-molecule inhibitors can be optimized to avoid triggering immunological responses and they are appropriate for treating metastatic tumors where local injection of chemotherapeutic agents is less efficacious. Because inhibitors identified by the present methods can target the extracellular dimerization arm, they can be effective against kinase inhibitor-resistant tumors that have acquired mutations in the kinase domain. In addition, inhibitors identified by the present methods have the potential to interfere with heterodimerization of the EGF receptor with other ErbB family members. Thus, this class of inhibitors should offer clinical benefits either by themselves or in combination with existing therapeutics.

Figure 4:
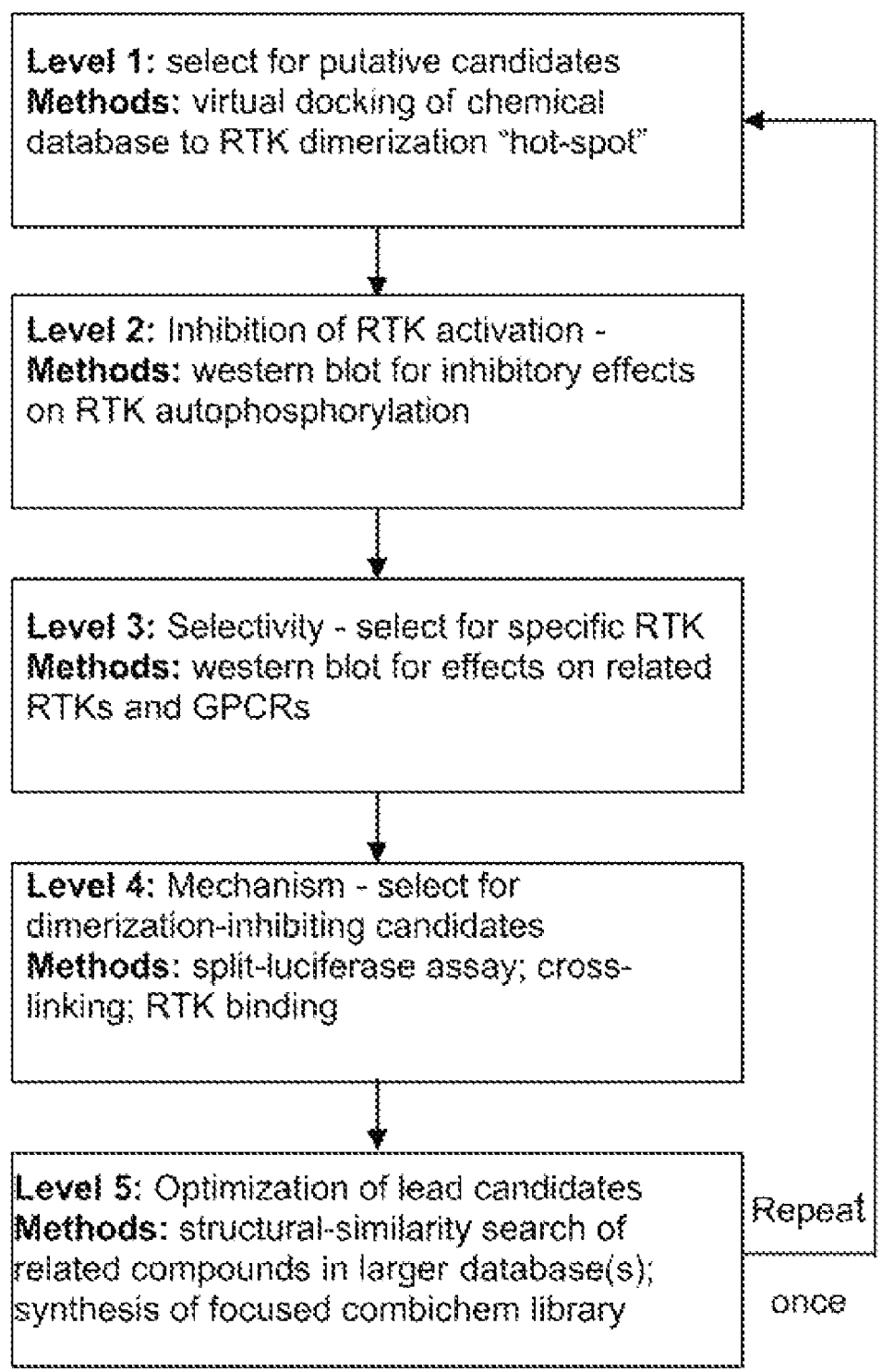
FIG. 4 illustrates an outline of methodology for identifying inhibitors of specific RTK signal transduction whose mechanism of action is by blocked dimerization of activated receptors.

In the present teachings, the dimerization interface of a particular RTK, such as, for example, EGFR, can be modeled and the binding site for the dimerization arm can be identified. This binding site can then be probed computationally by compounds from virtual libraries to identify potential inhibitors. The compounds identified either be purchased (if commercially available) or synthesized and tested for inhibition of tyrosine kinase activity (FIG. 4, example with EGFR) in an appropriate cell line expressing the RTK that is targeted. Active compounds can then be screened for selectivity against other RTKs on cells expressing those receptors. The mechanism of action of the inhibitors can be demonstrated by prevention of chemical cross-linking of the RTK receptor upon activation.

In some configurations, the present methods utilize vHTS (Virtual High-Throughput Screening). vHTS of the present teachings is an in silico protocol that generates a set of predicted receptor-inhibitor complexes, or binding poses, by docking a small molecule that are energetically complementary to the target site. The validity of each binding pose is assessed by a consensus score combining 11 scoring functions. The rationale of consensus scores is based on analyses that demonstrate improved performance in robustness of the protocol over any single scoring function alone. This docking-and-scoring process can be iterated for all compounds in the database, and subsequently, compounds can be ranked based on their consensus scores. The binding poses can be generated by software known to skilled artisans, such as Autodock 3.0 and 4.0 (Morris, G. M., et al., J. Computational Chemistry 19, 1639-1662, 1998) using the Lamarckian Genetic Algorithm implementation. The 11 scoring functions used to re-rank the post-docking binding poses include: Autodock, HP, HM, HS (implemented in X-score (Wang, R., et al., J. Computer-Aided Molecular Design 16, 11-26, 2002)). ChemSscore (Eldridge, M. D., et al., J. Computer-Aided Molecular Design 11, 425-445, 1997), Gold (Jones, G., et al., J. Mol. Biol. 267, 727-748, 1997), PMF (Muegge, I., J. Med. Chem. 49, 5895-5902, 2006), Drug-score (Gohlke, H., et al., J. Mol. Biol. 295, 337-356, 2000) (implemented in Sybyl), and Dfire (Zhang, C., et al., Proteins 60, 314-318, 2005). Various unique methods of consensing can be evaluated by testing model systems, and the best method based on those studies can be chosen for a vHTS protocol.

Some compounds described herein may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present teachings. In addition, the compounds disclosed herein may exist as tautomers and both tautomeric forms are encompassed by the scope of the present teachings, even though only one tautomeric structure is depicted or named.

When any variable (e.g. aryl, heterocycle, $R^4$, $R^6$ etc.) occurs more than one time in any substituent, its definition on each occurrence is independent at every other occurrence. Also, combinations of substituents and variables are permissible only if such combinations result in stable compounds.

It is understood that substituents and substitution patterns on the compounds of the present teachings can be selected by one of ordinary skill in the art to provide compounds that are chemically stable and that can be readily synthesized by techniques known in the art, as well as those methods set forth below, from readily available starting materials.

As used herein, "alkyl" is intended to include both branched and straight-chain aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, propyl, isopropyl, butyl, t-butyl, pentyl, hexyl, heptyl, octyl, nonyl, decyl, and so on.

"Cycloalkyl" as used herein is intended to include non-aromatic cyclic hydrocarbon groups, having the specified number of carbon atoms, which may or may not be bridged or structurally constrained. Examples of such cycloalkyls include, but are not limited to, cyclopropyl, cyclobutyl, cyclopentyl, cyclohexyl, adamantyl, cyclooctyl, cycloheptyl, tetrahydro-naphthalene, methylenecylohexyl, and the like.

If no number of carbon atoms is specified, the term "alkenyl" refers to a non-aromatic hydrocarbon radical, straight, branched or cyclic, containing from 2 to 10 carbon atoms and at least one carbon-to-carbon double bond. Preferably one carbon-to-carbon double bond is present, and up to 4 non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon-to-carbon triple bond. Up to 3 carbon-carbon triple bonds may be present. Thus, "$C_2$-$C_6$ alkynyl" means an alkynyl radical having from 2 to 6 carbon atoms. Alkynyl groups include ethynyl, propynyl and butynyl. As described above with respect to alkyl, the straight, branched or cyclic portion of the alkynyl group may contain triple bonds and may be substituted if a substituted alkynyl group is indicated.

As used herein, "aryl" is intended to mean any stable monocyclic or bicyclic carbon ring of up to 7 atoms in each ring, wherein at least one ring is aromatic. Examples of such aryl elements include phenyl, naphthyl, indanyl, indanonyl, indenyl, biphenyl, tetralonyl, tetralonyl, fluorenonyl, phenanthryl, anthryl, acenaphthyl, tetrahydronaphthyl, and the like.

As appreciated by those of skill in the art, "halo" or "halogen" as used herein is intended to include chloro, fluoro, bromo and iodo.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzimidazolyl, benzodioxolyl, benzotriazolyl, benzothiofuranyl, benzothiazolyl, furanyl, thienyl, benzothienyl, benzofuranyl, benzoquinolinyl, imidazolyl, isoquinolinyl, oxazolyl, isoxazolyl, indolyl, pyrazinyl, pyridazinyl, pyridinyl, pyrimidinyl, pyrrolyl, quinolinyl, tetrahydronaphthyl, tetrahydroquinoline, and the like.

The term heterocycle or heterocyclic or heterocyclyl, as used herein, represents a stable 5- to 7-membered monocyclic or stable 8- to 11-membered bicyclic heterocyclic ring which is either saturated or unsaturated, and which consists of carbon atoms and from one to tour heteroatoms selected from the group consisting of N, O, and S, and including any bicyclic group in which any of the above-defined heterocyclic rings is fused to a benzene ring. The heterocyclic ring may be attached at any heteroatom or carbon atom that results in the creation of a stable structure. "Heterocycle" or "heterocyclyl" therefore includes the previously mentioned heteroaryls, as well as dihydro and tetrahydro analogs thereof. Further examples of "heterocyclyl" include, but are not limited to the following: azepanyl, azetidinyl, benzimidazolyl, benzodioxolyl, benzofuranyl, benzofurazanyl, benzopyranyl, benzopyrazolyl, benzotriazolyl, benzothiazolyl, benzothienyl, benzothiofuranyl, benzothiophenyl, benzothiopyranyl, benzoxazepinyl, benzoxazolyl, carbazolyl, carbolinyl, chromanyl, cinnolinyl, diazepanyl, diazapinonyl, dihydrobenzofuranyl, dihydrobenzofuryl, dihydrobenzoimidazolyl, dihydrobenzothienyl, dihydrobenzothiopyranyl, dihydrobenzothiopyranyl sulfone, dihydrobenzothiophenyl, dihydrobenzoxazolyl, dihydrocyclopentapyridinyl, dihydrofuranyl, dihydroimidazolyl, dihydroindolyl, dihydroisooxazolyl, dihydroisoquinolinyl, dihydroisothiazolyl, dihydrooxadiazolyl, dihydrooxozolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxanyl, dioxidotetrahydrothienyl, dioxidothiomorpholinyl, furyl, furanyl, imidazolyl, imidazolinyl, imidazolidinyl, imidazothiazolyl, imidazopyridinyl, indazolyl, indolazinyl, indolinyl, indolyl, isobenzofuranyl, isochromanyl, isoindolyl, isoindolinyl, isoquinolinone, isoquinolyl, isothiazolyl, isothiazolidinyl, isoxazolinyl, isoxazolyl, methylenedioxybenzoyl, morpholinyl, naphthpyridinyl, oxadiazolyl, oxazolyl, oxazolinyl, oxetanyl, oxoazepinyl, oxadiazolyl, oxidothiomorpholinyl, oxodihydrophthalazinyl, oxodihydroindolyl, oxoimidazolidinyl, oxopiperazinyl, oxopiperidinyl, oxopyrrolidinyl, oxopyrimidinyl, oxopyrrolyl, oxotriazolyl, piperidyl, piperidinyl, piperazinyl, pyranyl, pyrazinyl, pyrazolyl, pyridazinyl, pyridinonyl, pyridopyridinyl, pyridazinyl, pyridyl, pyrimidinyl, pyrrolyl, pyrrolidinyl, quinazolinyl, quinolinyl, quinolyl, quinolinonyl, quinoxalinyl, tetrahydrocycloheptapyridinyl, tetrahydrofuranyl, tetrahydrofuryl, tetrahydroisoquinolinyl, tetrahydropyranyl, tetrahydroquinolinyl, tetrazolyl, tetrazolopyridyl, thiadiazolyl, thiazolyl, thiazolinyl, thienoluryl, thienyl, thiomorpholinyl, triazolyl, azetidinyl, 1,4-dioxanyl, hexahydroazepinyl, and the like. In some embodiments of the present teachings, a heterocycle can be selected from oxoazepinyl, benzimidazolyl, diazepanyl, diazapinonyl, imidazolyl, oxoimidazolidinyl, indolyl, isoquinolinyl, morpholinyl, piperidyl, piperazinyl, pyridyl, pyrrolidinyl, oxopiperidinyl, oxopyrimidinyl, oxopyrrolidinyl, quinolinyl, tetrahydrofuryl, tetrahydrofuranyl, tetrahydroisoquinolinyl, thienyl, furyl, furanyl, pyrazinyl, benzofuranyl, isoxazolyl, pyrrolyl, thiazolyl, benzothienyl, dihydroisoquinolinyl, azepanyl, thiomorpholinyl, dioxanyl, dioxidotetrahydrothienyl, imidazothiazolyl, benzothiazolyl, and triazolyl. In other embodiments of the present teachings, a heterocycle can be selected from benzofuranyl, thienyl, pyrrolyl, isoxazolyl, furyl, and pyridyl.

As used herein, "aralkyl" is intended to mean an aryl moiety, as defined above, attached through a $C_1$-$C_{10}$ alkyl linker, where alkyl is defined above. Examples of aralkyls include, but are not limited to, benzyl, naphthylmethyl and phenylpropyl.

As used herein, "heterocyclylalkyl" is intended to mean a heterocyclic moiety, as defined below, attached through a $C_1$-$C_{10}$ alkyl linker, where alkyl is defined above. Examples of heterocyclylalkyls include, but are not limited to, pyridylmethyl, imidazolylethyl, pyrrolidinylmethyl, morpholinylethyl, quinolinylmethyl, imidazolylpropyl and the like.

As used herein, the term "substituted $C_1$-$C_{10}$ alkyl" is intended to include the branch or straight-chain allyl group of the specified number of carbon atoms, wherein the carbon atoms may be substituted with 1 to 3 substituents selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$ ($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heterocycle, heterocyclylalkyl, halo-aryl, halo-arakyl, halo-heterocycle, halo-heterocyclylalkyl, cyano-aryl, cyano-aralkyl, cyano-heterocycle and cyano-hetcrocyclylalkyl.

As used herein, the terms "substituted $C_3$-$C_{10}$ cycloalkyl", "substituted aryl", and "substituted heterocyclyl", are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

As used herein, the phrase "substituted with at least one substituent" is intended to mean that the substituted group being referenced has from 1 to 6 substituents. Preferably, the substituted group being referenced contains from 1 to 3 substituents, in addition to the point of attachment to the rest of the compound.

In some embodiments, $R^1$ can be substituted or unsubstituted $C_1$-$C_6$ alkyl. In further embodiments, $R^1$ can be ethyl or tert-butyl.

In some embodiments, $R^2$ can be halogen, substituted or unsubstituted phenyl, or substituted or unsubstituted heterocyclyl, selected from pyridyl, benzofuranyl, isoaxazolyl, furanyl, pyrrolyl, and thienyl. In other embodiments, $R^2$ can be halogen or substituted or unsubstituted $C_2$-$C_{10}$ alkynyl. In further embodiments, $R^2$ can be halogen.

It is intended that the definition of any substituent or variable (e.g., $R^4$, $R^a$, n, etc.) at a particular location in a molecule be independent of its definitions elsewhere in that molecule. Thus, —$N(R^4)_2$ represents —NHH, —$NHCH_3$, —$NHC_2H_5$, etc. It is understood that substituents and substitution patterns on the compounds of the present teachings can be selected by one of ordinary skill in the art to provide compounds that are chemically stable and that can be readily synthesized by techniques known in the art, as well as those methods set forth below, from readily available starting materials.

For use in medicine, the salts of the compounds of Formula 1 through 4 will be pharmaceutically acceptable salts. Other salts may, however, be useful in the preparation of the compounds of the present teachings or of their pharmaceutically acceptable salts. When the compound of the present teachings is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium sodium, zinc and the like. Particularly preferred are the ammonium calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When a compound of the present teachings is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," J. Pharm. Sci., 1977:66:1-19.

It will also be noted that the compounds of the present teachings can be potentially internal salts or zwitterions, since under physiological conditions a deprotonated acidic moiety in the compound, such as a carboxyl group, may be anionic, and this electronic charge might then be balanced internally against the cationic charge of a protonated or alkylated basic moiety, such as a quaternary nitrogen atom.

The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor. NY, 1999. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. As used in the present description and the appended claims, the singular forms "a", "an" and "the" are intended to include the plural forms as well, unless the context indicates otherwise.

In the Examples below, experiments can involve one or more of the following materials and methods.

Virtual Screening: Autodock 4.0 (Huey, R., et al., J. Comput. Chem. 28, 1145-1152, 2007; Morris, G. M., et al., J. Comput. Chem., 19, 1639-1662, 1998) was used to screen the NCI-diversity database (1990 compounds). The database was initially downloaded from the Autodock website and processed by in-house scripts to fix incorrectly formatted structures, and to exclude structures that contained metals: iron, zinc, mercury and copper (final size=1926 compounds). A docking box of dimension 25 ÅA3 was centered at the Tyr-246/Tyr-Y251 recognition site on monomer A of the extracellular dimer crystal structure (PDB: 1 MOX). Larmackian genetic algorithm with Solis and Wets local search was used to generate 100 docking poses per compound. All poses were subsequently scored using: HP, HM, HS (implemented in X-score 1.2.1 (Wang et al., J. Comput. Aided Mol. Des. 16, 11-26, 2002), D-score, PMF, G-score, Chem-score (implemented in Sybyl 7.3 CSCORE module), and Dfire (Zhang et al., J. Med. Chem. 48, 2325-2335, 2005). A consensus score for each pose was calculated by summing the rankings given by each of the 8 scoring functions. Three compounds that were ranked high using the consensus scores were excluded because they displayed high rankings against many other protein targets suggesting poor specificity.

EGF receptor autophosphorylation: CHO cells stably expressing wild type EGF receptor were grown to 80% confluency in 35 mm plates in Hams' F-12 containing 10% fetal bovine serum (FBS), penicillin/streptomycin, and 100 μg/ml hygromycin. Prior to use, the cells were incubated for 3 hours in F-12 medium containing 0.1% FBS. For the experiments, cultures were incubated with the test compounds at a final concentration of 100 μM in 1% DMSO for 30 min at 25° C. in F-12 containing 1 mg/ml bovine serum albumin and 25 mM Hepes, pH 7.2. Control cultures were incubated for the same length of time with 1% DMSO. EGF (Biomedical Technologies, Inc) was then added at a final concentration of 3 nM and the cultures incubated at 25° C. for an additional 1 min. Subsequently, the monolayers were washed twice with ice-cold phosphate-buffered saline and scraped into RIPA buffer (10 mM Tris, pH 7.2, 150 mM NaCl, 0.1% sodium dodecyl sulfate, 1% Triton X-100, 17 mM deoxycholate, and 2.7 mM EDTA) containing 1 mM sodium orthovanadate, 20 mM p-nitrophenylphosphate, and protease inhibitors. Equal amounts of protein (BCA assay, Pierce) were separated by electrophoresis on a 9% SDS polyacrylamide gel, and transferred to PVDF or nitrocellulose (Millipore). Western blotting was performed using anti-pY1 173 (Cell Signaling), or anti-EGF receptor antibodies (Cell Signaling and Santa Cruz). Time-course and dose-response experiments were done using the same procedure except that the dose or preincubation time with inhibitors was varied. A similar protocol was used for assessing insulin-stimulated phosphorylation of IRS-1 or PDGF-stimulated receptor autophosphorylation except that differentiated 3T3-L1 cells or NIH3T3 cells were used, respectively. In all cases, phosphorylation was quantified using ImageJ and normalized to that observed in control samples.

Chemical cross-linking of the EGF receptor: CHO cells stably expressing EGF receptor were preincubated with the test compounds for 15 min at a final concentration of 100 µM. EGF (25 nM) was then added for 3 min followed by the addition of $BS^3$ (Pierce) at a final concentration of 3 mM for 30 min. The reaction mixture was buffered at pH 8. The cross-linking reactions were quenched by the addition of glycine to a final concentration of 1 M (pH 7.5). Cells were lysed as above, and equal amounts of protein were loaded onto a 4%-7.5% gradient SDS-polyacrylamide gel. After electrophoresis and transfer to PVDF, EGF receptor dimerization was measured by Western blotting using anti-EGF receptor antibodies.

Luciferase fragment complementation imaging: CHO-K1 Tet-On cells stably expressing ΔC-EGFR-NLuc and ΔC-EGFR-CLuc (Yang, K. S., et al., J. Biol. Chem. 284, 7474-7482, 2009) were plated 48 hrs prior to imaging in DMEM containing 1 µg/ml doxycycline. On the day of imaging, cells were serum-starved for 4 hrs followed by treatment with vehicle, the indicated concentration of each compound, or 1 µg/ml cetuximab for 20 min in the presence of 0.6 mg/ml Dluciferin. 3 nM EGF was then added and the photon flux immediately measured using an IVIS imaging system. Data represent the change in photon flux between EGF-treated cells and control cells. For the control experiments using the FRB-NLuc and CLuc-FKBP system (Luker et al., Proc. Natl. Acad. Sci. USA 101, 12288-12293, 2004; Villalobos et al., Genomics Protocols, Vol. 439. Humana Press, pp 339-352, 2008), CHO-K1 Tet-On cells were plated 48 hrs prior to use and transiently transfected with the cDNA encoding FRB-NLuc and CLuc-FKBP 24 later. On the day of assay, cells were pre-treated with vehicle or 80 nM rapamycin for 4 hrs. Media was removed and replaced with DMEM lacking phenol red containing 0.6 mg/ml D-luciferin and DMSO, 25 µM compound NSC11241, or 25 µM compound NSC56452. Photon flux was measured as above.

$^{125}$I-EGF binding: $^{125}$I-EGF binding was carried out by incubating the cells with 50 pM $^{125}$I-EGF for 24 hr at 4° C., following the previously described protocol (Macdonald & Pike, Proc. Natl. Acad. Sci. USA 105, 112-117, 2008).

Cell Growth Assay: HeLa cells were grown in Dulbecco's Modified Eagles' Medium with 10% FBS. Cells were plated in triplicate in 96-well plates at 5000 cells per well and allowed to grow for 24 hours before the addition of DMSO (control), erlotinib (Genetech) or NSC56452. All cultures contained 1% DMSO in the final media. Cells were then incubated for 48 hours. The cell growth rate was then measured using the cellTiter 96 Aqueous One Solution Cell Proliferation Assay kit according to the manufacturer's instructions (Promega). Readings were taken at 490 nm after 1 hour incubation with the MTS and PMS solution.

EXAMPLES

The following examples are illustrative and are not intended to be limiting of any claim.

Example 1

Figure 5:
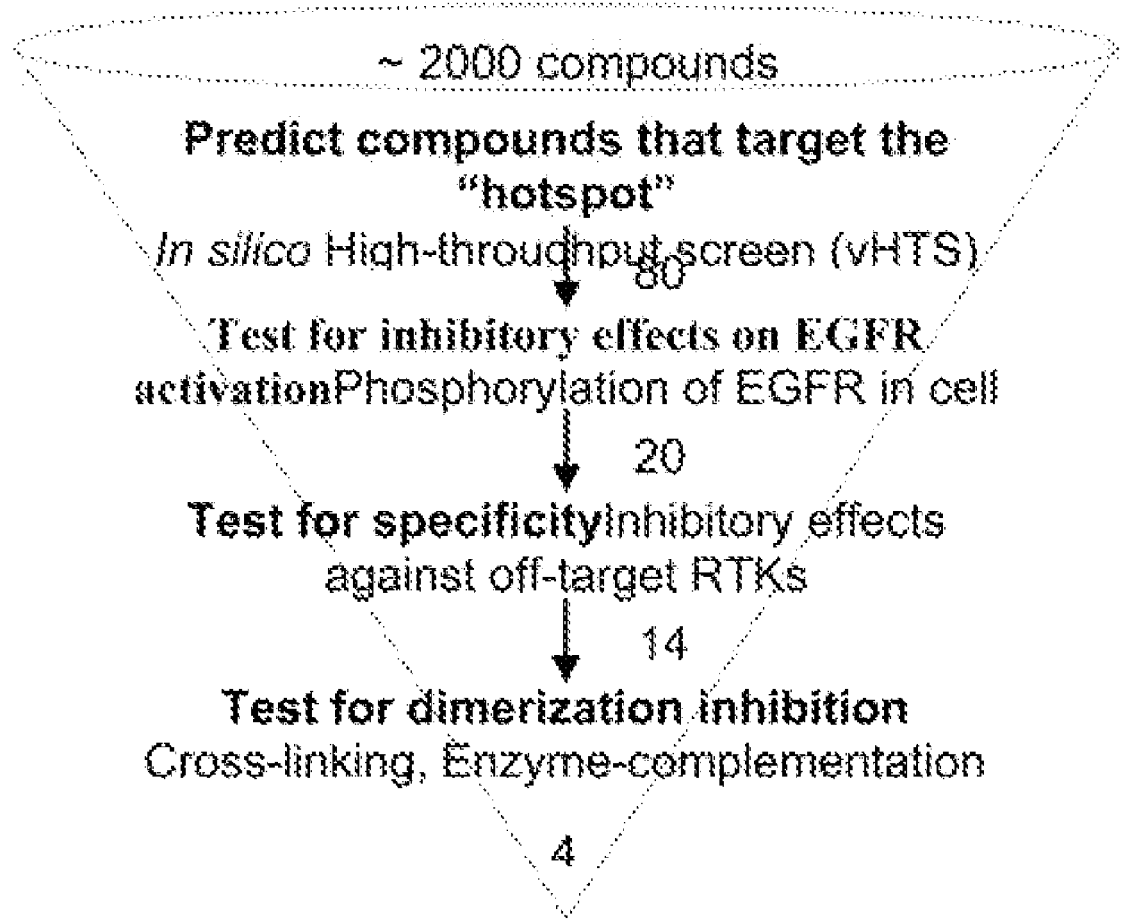
FIG. 5 illustrates a "top-down" approach which was used to identify 4 lead inhibitors of EGFR dimerization from a 2000-member library.

In some configurations, the present teachings disclose a "top down" approach to discovering new compounds which inhibit dimerization of an RTK such as EGFR (FIG. 5).

Figure 6:
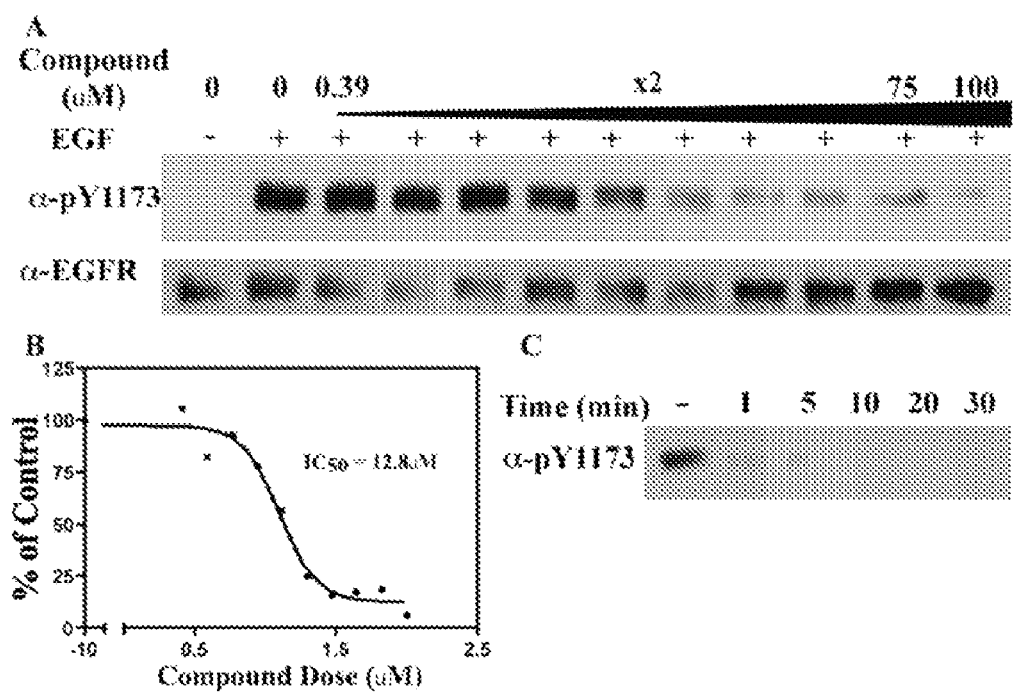
FIG. 6 illustrates the effects of a lead inhibitor compound, NSC11241, on EGF-induced phosphorylation.

In this example, approximately 2000 compounds are analyzed in an in silico high-throughput screen for predicted interactions with an EGFR extracellular domain dimer. This screen identifies 80 compounds. These 80 compounds are tested for inhibitory effects on activation of an RTK such as EGFR in an assay on the effects of the compounds on EGFR phosphorylation in a cell (FIG. 6; see Example 2). The 20 compounds showing the most favorable results from these assays are then tested for specificity, by testing for inhibitory effects of the compounds against other, "off-target" RTKs. The 14 most promising compounds remaining after these assays are then tested in assays on mechanism, including an assay on each compound's ability to inhibit chemical cross-linking of an EGFR when the EGFR is stimulated with a natural ligand, and an enzyme-complementation assay. Such an investigation yields 4 lead compounds as useful inhibitors of EGFR dimerization.

Example 2

This example illustrates the effects of a lead inhibitor on EGFR-induced phosphorylation.

In this example (FIG. 6) compound NSC11241 is tested for A) Dose-dependent inhibition of the compound versus EGFR phosphorylation. The controls (lanes 1 and 2) are treated with 1% DMSO. Doses are increased 2 fold in each successive lane from 0.39 µM to 100 µM. B) Estimate of $IC_{50}$ value; C) Inhibition effects of various pre-incubation time, the control (lane 1) is treated with 1% DMSO for 30 minutes. The data show the inhibitory effect of compound NSC11241 on EGFR phosphorylation.

Citations for assays used:
1. Phosphorylation Assay: Macdonald, J., et al., Biochim Biophys Acta 1763, 870-878, 2006.
2. PDGFR Specificity Test: Nakata, S., et al., J. Biol. Chem. 282: 37815-37825, 2007.
3. Insulin-Receptor Specificity Test: Semenkovich, C. F., J. Biol. Chem. 264: 9030-9038, 1989.
4. Cross-linking of TKRs: Gan, H. K., J. Biol. Chem. 282, 2840-2850, 2007.

Example 3

This example illustrates datasets used for evaluation and specification of consensus scoring function of vHTS:

Lead PDB is the PDB file from which the target protein receptor was used for cross-docking.

Plasmepsin II (aspartic protease from *Plasmodium falciparum*)
  Lead PDB: 1LEE
  Lead citation: Asojo, O. A., et al., Acta Crystallogr., Sect. D 58: 2001-2008, 2002
  Reported $K_i$: 0.018 µM
  Other PDRs used: 1LF2, 1LF3, 1M43, 1ME6, 1W6H, 1W6I, 1XE5, 2BJU, 2IGX, 2IGY.

CDK2 (cyclin dependent protein kinase 2)
  Lead PDB: 2B54
  Lead citation: Markwalder, J. A., et al., J. Med. Chem. 47: 5894-5911, 2004
  Reported $K_i$: 0.02 µM
  Other PDBs used: 1AQ1, 1CKP, 1DI8, 1DM2, 1E1V, 1E1X, 1E9H, 1FVT, 1G5S, 1GIH, 1GZ8, 1H00, 1H01, 1H07, 1H08, 1H0V, 1HOW, 1H1P, 1H1Q, 1H1R, 1H1S, 1JSV, 1JVP, 1KE5, 1KE6, 1KE7, 1KE8, 1KE9, 1OGU, 1OI9, 1OIQ, 1OIR, 1OIT, 1OIU, 1OIY, 1P2A, 1P5E, 1PF8, 1PKD, 1PXI, 1PXK, 1PXL, 1PXM, 1PXN, 1PXO, 1PXP, 1PYE,

1R78, 1URW, 1V1K, 1VYW, 1VYZ, 1W0X, 1WCC, 1Y91, 2A4L, 2B52, 2B53, 2B55, 2BPM

ER (Estrogen Receptor)
    Lead PDB: 1XPC
    Lead citation: Blizzard, T. A., et al., Bioorg. Med. Chem. Lett. 15, 107-113, 2005.
    Reported $K_i$: 0.0017 µM
    Other PDBs used: 1A52, 1ERR, 1L2I, 1SJ0, 1UOM, 1X7E, 1X7R, 1XP1, 1XP6, 1XP9, 1XQC, 1YIM, 1YIN, 1ZKY, 2FAI, 2BIV, 2AYR, 3ERD, 3ERT Hsp90 (heat shock protein90)
    Lead PDB: 2BRC
    Lead citation: Cheung, K. M., et al., Bioorg. Med. Chem. Lett. 15, 3338-3343 2005.
    Reported $K_i$: 7.1 µM
    Other PDBs used: 1A4H, 1AH8, 1BGQ, 1YC1, 1YC3, 1YC4, 1ZW9, 2BRE, 2CGF Example 4

This example illustrates consensus scoring:

Different ways of combining scores from the eleven scoring function were evaluated. Of the most notables: 1) by sum of ranking, 2) by sum of raw voting (with top 10% cut-off), 3) by sum normalized voting (95% confidence interval), and 4) by sum of normalized scores.

For each of the above methods, all possible permutations to combine the scores were also tested and evaluated to determine the best combinations of scores to include. In addition, a weighting factor between 0 and 1 were tried for each scores at 0.2 increments to determine the optimal weighting to associate with each scores. The method that sums-up rankings (method 1 above) with equal weighting factors and includes all functions, offered the best performance at that time. Briefly, a given docked pose was ranked among all poses of all compounds by each of the 11 scoring functions. The 11 resultant ranks are then tallied up with equal weighting to calculate the consensus score.

Example 5

This Example illustrates virtual high-throughput screening protocols.

The vHTS employed in these experiments used AutoDock 4.0 (Huey, R., et al., J. Comput. Chem. 28, 1145-1152 2007; Morris, G. M., et al., J. Comput. Chem. 19, 1639-1662, 1998) to dock approximately 2000 compounds present in the NCI Diversity database to a 25 Å$^3$ docking box centered on the Tyr-246/Tyr-251 recognition pocket of the dimerization arm of the EGF receptor. A total of 8 scoring functions were used to independently rank all predicted docking poses, and the final ranking was taken as the consensus rank.

The enrichment of a typical vHTS protocol is measured by its ability to recover true positives as early in the rankings as possible from a compound library. Evaluation of a protocol thus depends on the availability of existing reference active compounds. Because there were no existing inhibitors that targeted the Tyr-246/Tyr-251 site, it was not possible to evaluate the enrichment power of our vHTS protocol for the EGF receptor system a priori. As a result, robustness, measured as the average enrichment across different protein targets, became a critical criterion for evaluating the performance of the protocol to be used. The protocol was applied to four different protein targets: plasmepsin II (PMII), human cyclin-dependent kinase 2 (Cdk2), estrogen receptor (ER), and yeast heat shock protein (Hsp90). These proteins have multiple co-crystal complex structures bound to structurally diverse ligands in the PDB, and these ligands (true positives) were mixed with 1926 decoy compounds (negatives) to form the testing compound library.

The ability of the vHTS protocol to recover known ligands from this library was evaluated using enrichment curve analysis (Chen, H., et al., J. Chem. Inf. Model 46, 401-415, 2006).

Figure 7:
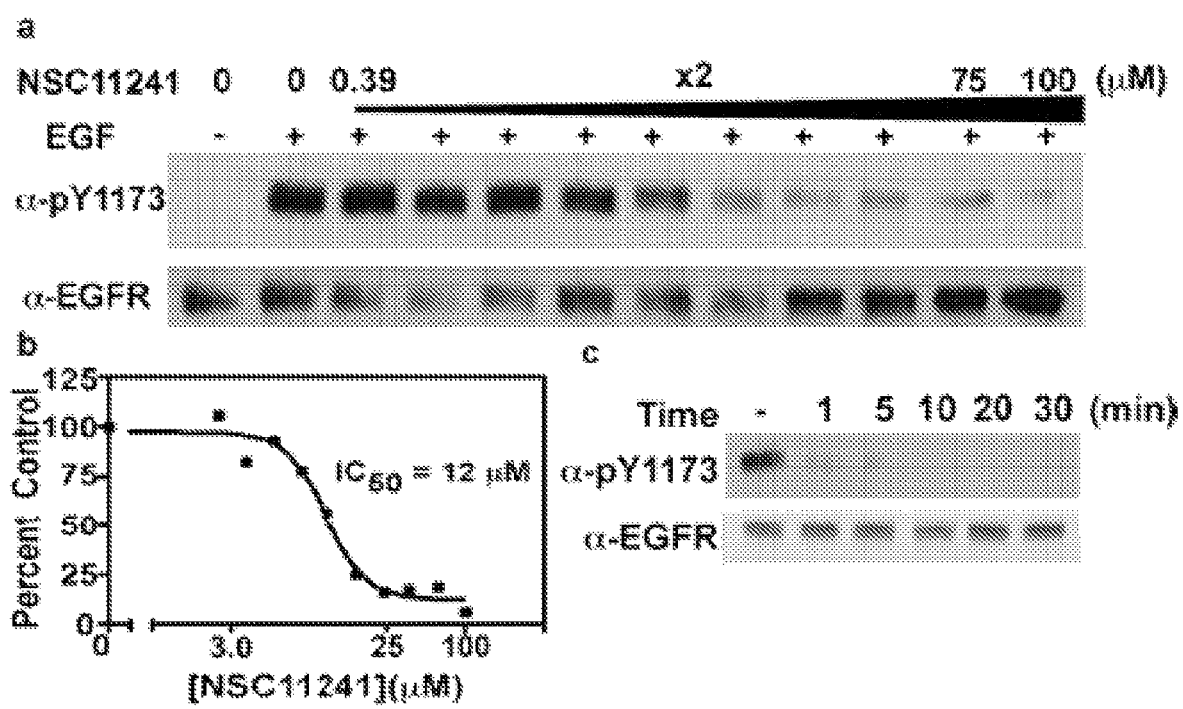
FIG. 7 illustrates evaluation of the vHTS protocol against four testing cases shown in an enrichment curve analysis. In each case, multiple known ligands were mixed in with ~2000 random compounds to form the screening library. The black diagonal line represents the random distribution of active molecules.

As shown in the Table 2 and FIG. 7, the protocol recovered at least one true ligand within the top 1% of the ranked library for PMII, Cdk2, and ER, and within the top 10% of the library for Hsp90. On average, this protocol is expected to recover at least one true ligand within the top 3.5%, and nearly ⅔ of all ligands within the top 15% of the representative libraries.

TABLE 2

Efficacy and robustness of the vHTS protocol.

| Targets | Coverage$_{1\%}$[1] | Coverage$_{15\%}$ | Coverage$_{30\%}$ | Coverage$_{50\%}$ | Best[2] |
|---------|---------------------|-------------------|-------------------|-------------------|---------|
| Cdk2    | 3%                  | 49%               | 67%               | 100%              | 0.05%   |
| PMII    | 60%                 | 100%              | 100%              | 100%              | 0.65%   |
| ER      | 69%                 | 81%               | 94%               | 100%              | 0.05%   |
| HSP90   | 0%                  | 20%               | 60%               | 100%              | 13.21%  |
| Avg     | 33%                 | 63%               | 80%               | 100%              | 3.5%    |

[1]Coverage$_{fraction}$ = Number of known actives recovered within the given fraction of the database/Total number of actives present in the database × 100%
[2]Best = ranking of the best predicted active/database size × 100%

Example 6

This example illustrates inhibition of EGF receptor activation as the first-pass screen.

In these experiments, we applied the vHTS protocol to the EGF receptor and obtained samples of the 80 top-ranked compounds (top 4%) along with 40 randomly chosen compounds from NCI for testing. Of the 80 compounds, 4 were not soluble in water or dimethylsulfoxide (DMSO), and, therefore, not pursued further. The remaining 76 compounds were tested for their ability to inhibit EGF-stimulated receptor autophosphorylation at a concentration of 100 µM.

Tyr-1173 is a major site of autophosphorylation in the EGF receptor (Zhou, M. M., et al., J. Biol. Chem. 270, 31119-31123, 1995). Of the 76 compounds tested, 20 produced a significant (>60%) decrease in the level of Tyr-1173 phosphorylation without affecting the level of EGF receptors. FIG. 6 presents typical results for the characterization of a lead inhibitor. In all cases, the inhibition by the lead compounds was dose-dependent, with IC$_{50}$ values ranging from a low of 400 nM to a high of 24 µM (FIG. 6a and FIG. 6b). Inhibition was rapid with some compounds requiring as little as 1 minute of preincubation time to achieve maximal inhibition of receptor phosphorylation (FIG. 6c). None of the set of 40 compounds randomly chosen from the same library inhibited receptor phosphorylation under the same conditions.

Example 7

This example illustrates specific inhibition of the EGF receptor activation by lead compounds.

Figure 8:
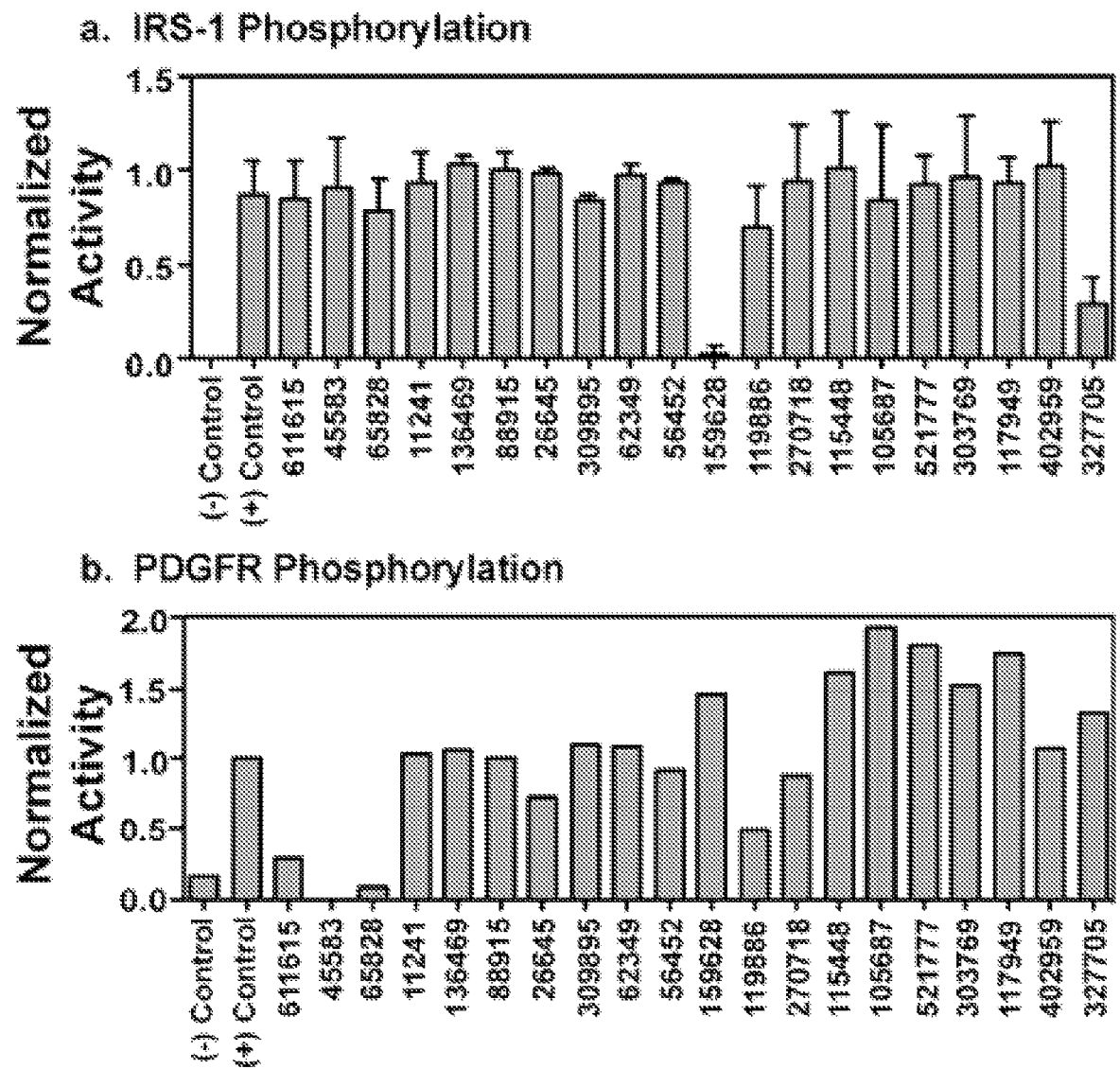
FIG. 8 illustrates specificity of inhibitors. Cells expressing either the insulin receptor or the PDGF receptor were pre-incubated with 1% DMSO (controls) or 100 μM of each of the 20 lead compounds. a) Insulin receptor kinase activity was assessed by measuring the phosphorylation of IRS-1 in response to 3 nM insulin for 1 minute. Data represent 3 independent experiments. b) PDGF receptor kinase activity was assessed by measuring autophosphorylation of the PDGF receptor in response to 2 nM PDGF for 3 minutes.

To assess the specificity of the 20 lead inhibitors, they were tested for their ability to inhibit two related receptor tyrosine kinases, the insulin receptor and the PDGF receptor. For the insulin receptor, insulin-stimulated tyrosine phosphorylation of IRS-1 in differentiated 3T3-L1 cells was assessed (Semenkovich, C., et al., J. Biol. Chem. 264, 9030-9038, 1989). For the PDGF receptor, PDGF-stimulated receptor autophosphorylation in NIH3T3 cells was measured (Nakata, S. et al., J. Biol. Chem. 282, 37815-37825, 2007). Neither 3T3-L1 cells nor NIH3T3 cells express the EGF receptor obviating potential problems associated with receptor crosstalk. The data in FIG. 8 demonstrate that of the 20 compounds that inhibit EGF receptor autophosphorylation, only 2 inhibit insulin-stimulated IRS-1 phosphorylation and 4 others inhibit PDGF receptor autophosphorylation. An additional 3 compounds that markedly enhanced PDGF receptor autophosphorylation were not pursued further.

Example 8

This example illustrates inhibition of EGF receptor dimerization by lead compounds.

Figure 9:
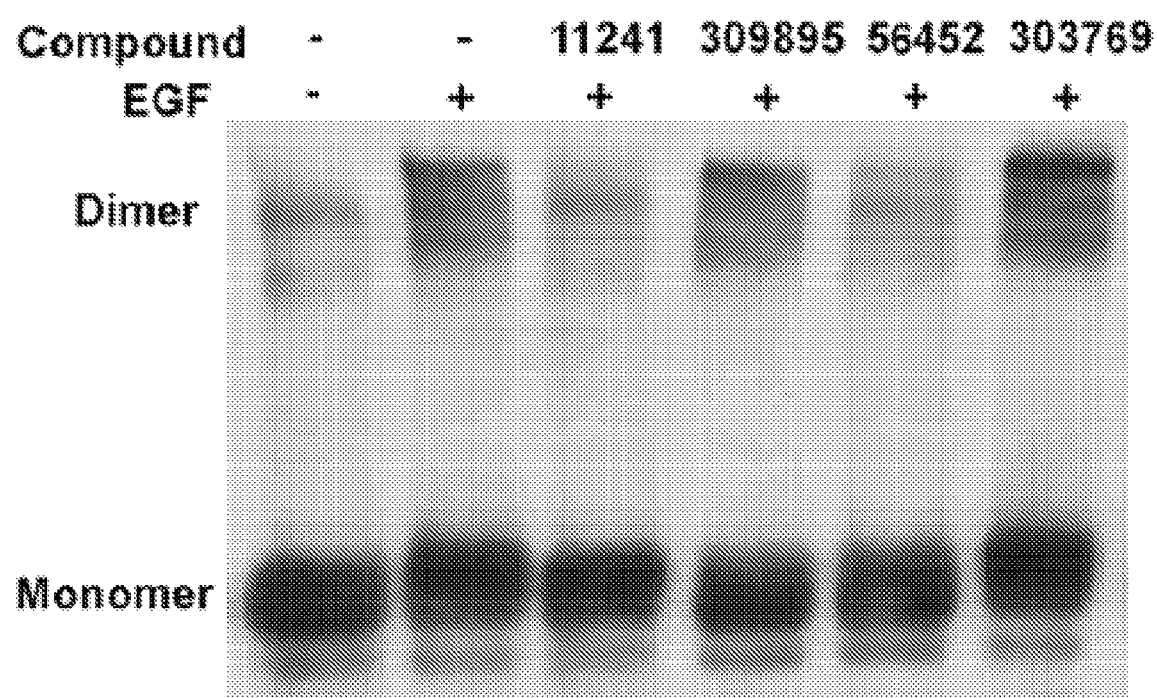
FIG. 9 illustrates inhibition of EGF receptor dimerization determined by a chemical cross-linking assay. Cells were pre-incubated with 1% DMSO (lane 1 and 2) or 100 μM of lead inhibitors (lane 3-6) prior to stimulation with 25 nM EGF (lane 2-6) for 5 minutes. All cells were then treated with 3 mM of the cross-linking reagent $BS^3$. The data show that NSC11241 (lane 3) and NSC56452 (lane 5) significantly inhibit dimer formation. Lane 4 and 6 show compounds that did not inhibit dimer formation.

Since the lead inhibitors were initially chosen based on their potential to interfere with EGF receptor dimerization, we next tested whether the remaining 11 candidates inhibited EGF receptor autophosphorylation by directly blocking receptor dimerization, as measured by chemical crosslinking. Cells were preincubated with the inhibitors for 15 min at a final concentration of 100 µM. EGF at 25 nM was then added followed by 3 mM bis(sulfosuccinimidyl)suberate ($BS^3$), a membrane impermeable chemical crosslinker. FIG. 9 shows the effect of a subset of these inhibitors on EGF receptor dimerization.

NSC11241 and NSC56452 significantly reduced the formation of high molecular weight dimers of the stimulated receptor while NSC309895 and NSC303769 failed to block dimer formation. None of the other compounds had any effect on the crosslinking of EGF receptor dimers. Because the crosslinker was used at a concentration 30-fold higher than that of the inhibitors (3 mM vs. 100 µM), it is unlikely that this inhibition was due to quenching of the crosslinking reaction by the compounds. Consistent with this conclusion, increasing the concentration of $BS^3$ to 5 mM yielded the same results. It is possible, however, that false negatives could be obtained if reaction of the compound with crosslinker prevented that compound from binding to the EGF receptor.

To further test the hypothesis that these lead compounds target EGF receptor dimer formation, NSC11241 and NSC56452 (FIG. 10*a*) were tested in a luciferase fragment complementation assay for EGF receptor dimerization (Yang, K. S., et al., J. Biol. Chem. 284, 7474-7482, 2009). For this assay, an EGF receptor lacking the entire intracellular domain (referred to as ΔCEGFR) was fused to either the N-terminal (NLuc) or the C-terminal (CLuc) fragments of firefly luciferase. Ligand-induced dimerization of ΔC-EGFR brings the luciferase fragments into close proximity resulting in enzyme complementation. The rate and extent of receptor dimerization can therefore be measured by following photon flux. The absence of the intracellular domain of the EGF receptor from these constructs ensures that compounds affecting luciferase activity do not do so by binding to the cytoplasmic portion of the receptor.

Figure 10:
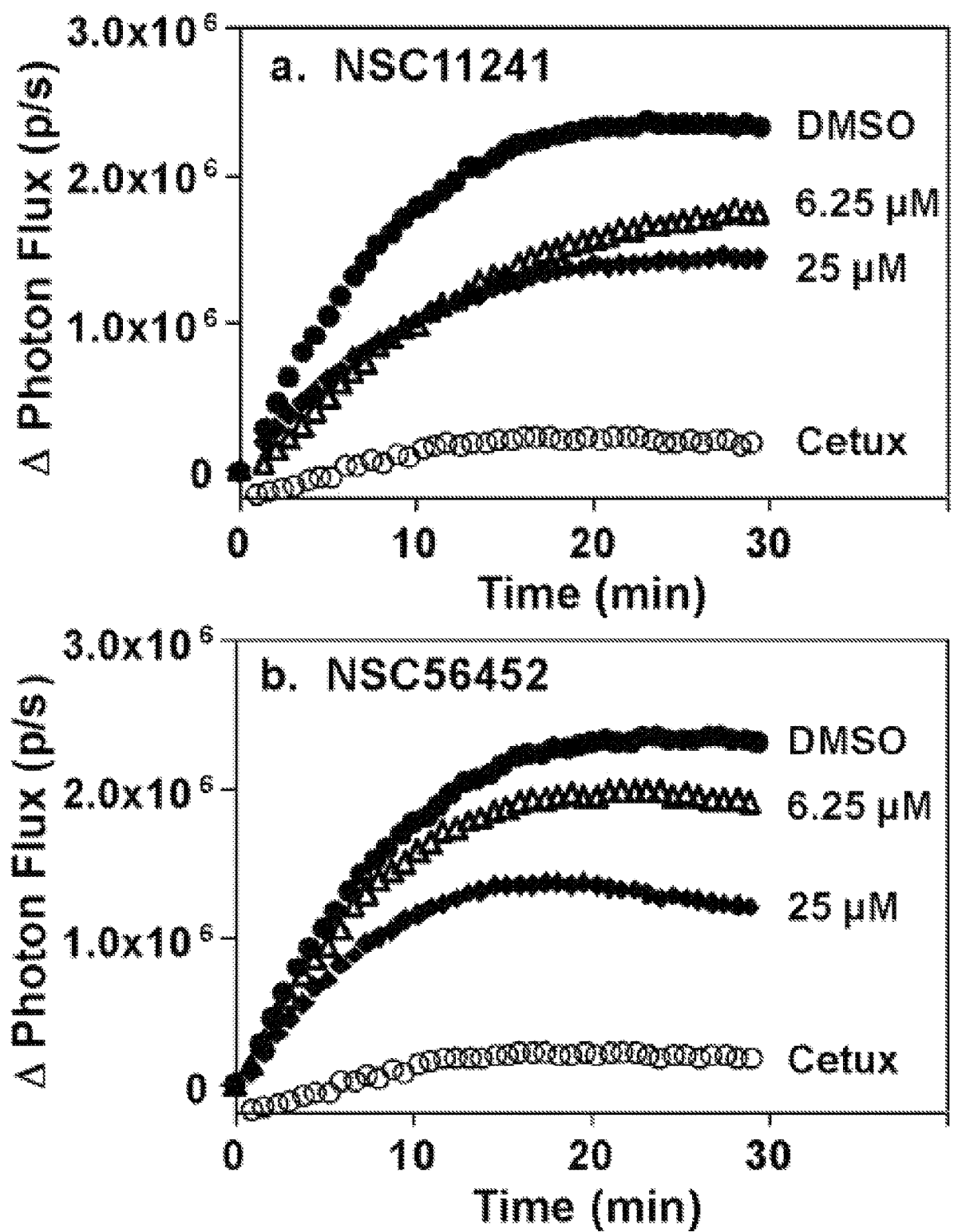
FIG. 10 illustrates inhibition of EGF receptor dimerization assayed by a luciferase fragment complementation. Cells stably expressing ΔC-EGFR-NLuc and ΔC-EGFR-CLuc were pre-treated with DMSO, the indicated concentrations of compounds or 1 μg/ml erbitux for 20 min in the presence of 0.6 mg/ml D-luciferin prior to the addition of 3 nM EGF. Data represent the change in photon flux between quadruplicates of EGF-treated and untreated control cells. a), NSC11241; b), NSC56452.
Figure 11:
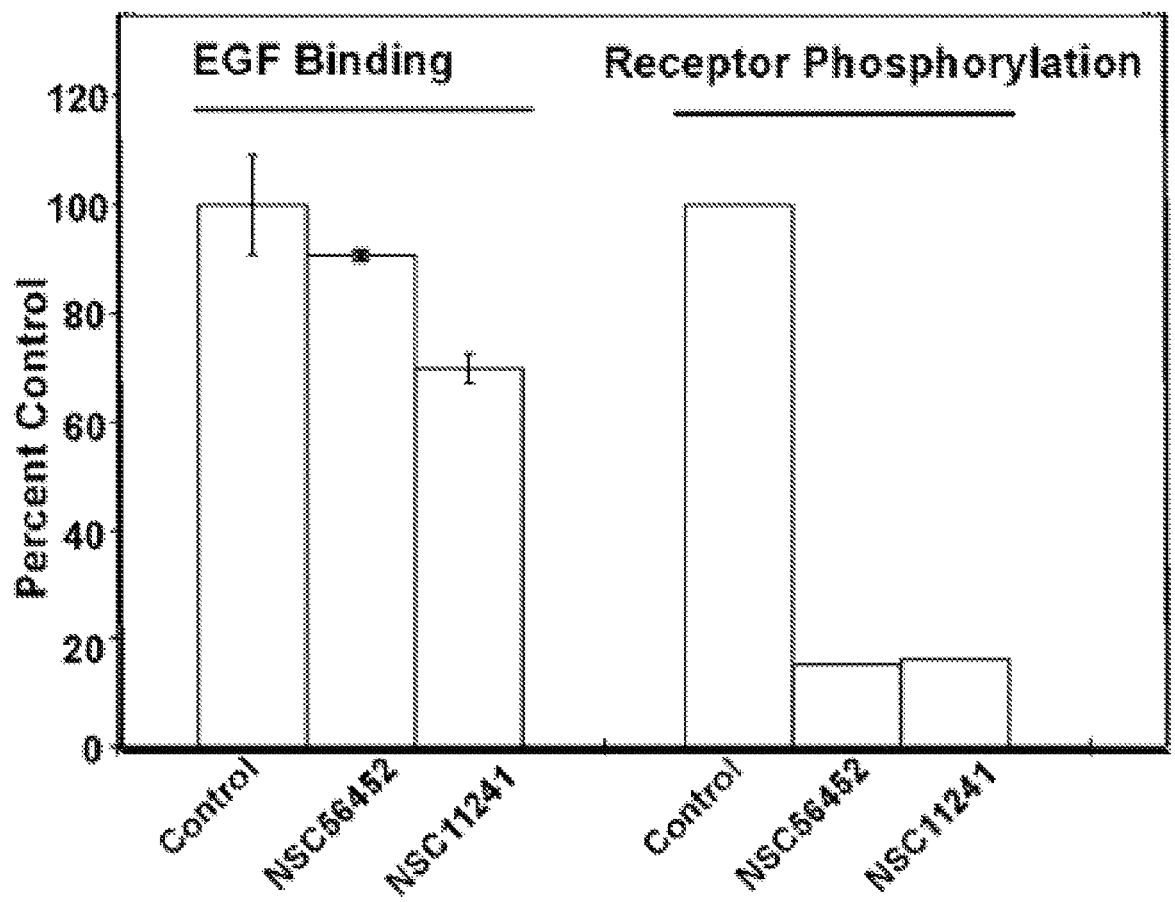
FIG. 11 illustrates effects of NSC56452 and NSC11241 on $^{125}$I-EGF binding and EGF receptor autophosphorylation. $^{125}$I-EGF binding and EGF receptor autophosphorylation were assessed as described in text. NSC56452 was tested at 100 μM while NSC11241 was used at 25 μM due to its limited solubility at 4° C., the temperature at which the binding assay was performed.

As shown in FIG. 10*a* and FIG. 10*b*, EGF stimulated a rapid increase in light production in control cells consistent with ligand-induced dimer formation. Cetuximab, an FDA-approved antibody-based drug that binds to the extracellular domain of the EGF receptor (Kirkpatrick, P., et al., 2004; Li et al., 2005), dramatically decreased EGF-induced luciferase activity, serving as a positive control of inhibition. In this system, NSC11241 (FIG. 10*a*) and NSC56452 (FIG. 10*b*) each induced a dose-dependent decrease in luciferase complementation compared to controls (FIG. 11). To exclude the possibility that the compounds simply inhibited complementation of the luciferase fragments, NSC11241 and NSC56452 were tested for their effect on CHO cells expressing FRBNLuc and its binding partner CLuc-FKBP. These proteins form a tight complex in the presence of rapamycin, resulting in an increase in luciferase complementation (Luker et al., Proc. Natl. Acad. Sci. USA 101, 12288-12293, 2004). No change in luciferase complementation was observed in cells treated with 25 µM NSC56452 or 25 µM NSC11241 compared to cells treated with rapamycin alone.

Example 9

This example illustrates that NSC56452 and NSC11241 do not inhibit by interfering with the binding of EGF ligands.

It was still possible that NSC56452 or NSC11241 might inhibit EGF receptor activation by interfering with the binding of EGF to the extracellular domain of the receptor. To address this possibility, we assessed the ability of $^{125}$I-EGF to bind to EGF receptor-expressing CHO cells in the absence and presence of these compounds. As shown in FIG. 11, NSC56452 had little effect on EGF binding but still significantly inhibited EGF receptor phosphorylation. Likewise, NSC11241 had only a modest effect on EGF binding but almost completely inhibited receptor autophosphorylation. These data indicate that neither of these compounds is likely to exert its inhibitory effect predominantly by blocking the binding of EGF to its receptor.

Example 10

This example illustrates growth inhibition of HeLa cells by NSC56452.

Figure 12:
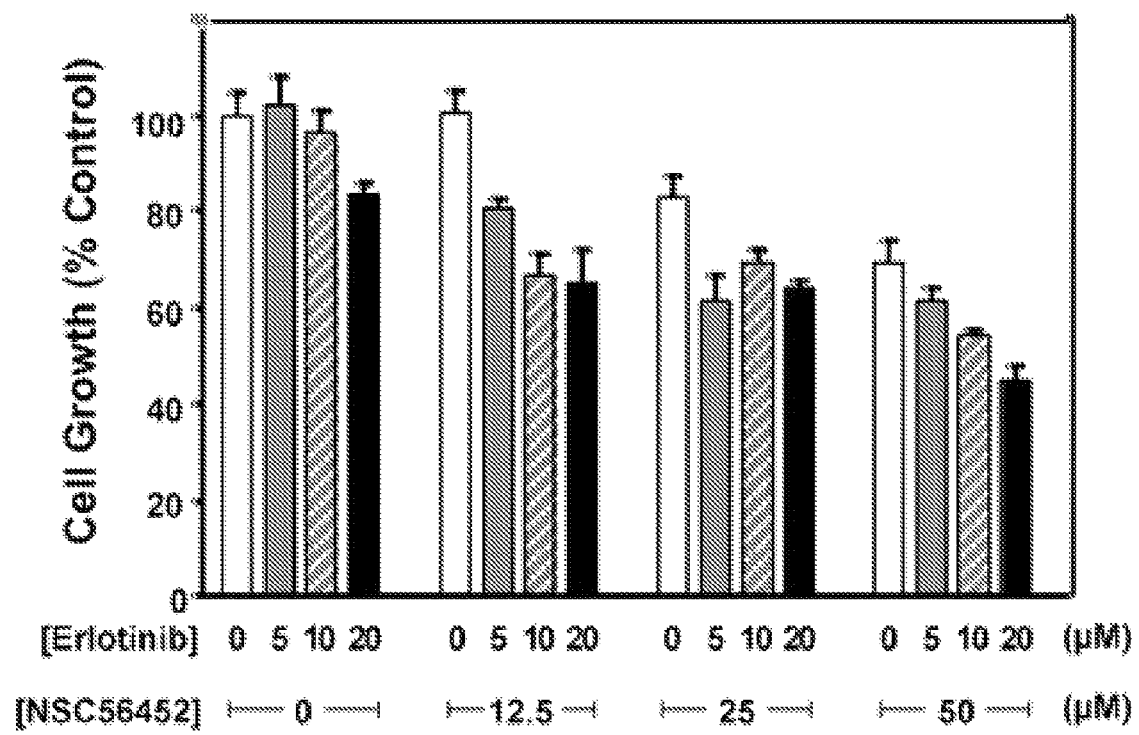
FIG. 12 illustrates inhibition of HeLa cell growth. Cells were grown in the absence or presence of erlotinib, NSC56452, or a combination of the two inhibitors at the indicated doses. Cell growth was measured by the cell Titer 96 Aqueous One Solution Cell Proliferation Assay after 48 hr incubation with the inhibitors. All experiments were performed in triplicates. All cultures contained 1% DMSO.

To assess the effect of the inhibitors on the growth of cancer cells, NSC56452 was tested for its ability to inhibit the proliferation of HeLa cells that express endogenous EGF receptors. The other inhibitor, NSC11241, was highly colored and hence could not be readily analyzed using the MTS cell-proliferation assay due to overlap in absorption spectra. In the absence of NSC56452, the tyrosine kinase inhibitor, erlotinib, showed only weak inhibition of cell proliferation at the doses tested. Similarly, by itself, NSC56452 showed a modest, dose-dependent inhibition of cell growth (FIG. 12, open bars). However, when NSC56452 was combined with a sub-maximal dose of erlotinib, greater inhibition of proliferation was observed than when either inhibitor was used alone at the equivalent dose (dark bars). These finds are consistent with the hypothesis that these two compounds inhibit EGF receptor activity through different mechanisms.

Example 11

This example illustrates reproducibility and scale-up of vHTS.

Encouraged by the virtual screening success, we further implemented a scaled-up vHTS infrastructure aimed at screening larger libraries. We developed a grid-based vHTS protocol using the X-grid technology (http://www.apple.com/server/macosx/technology/xgrid.html) to utilize distributed computing resources on the OpenMacGrid Network (http://www.macresearch.org/openmacgrid). The concept mirrors that of Folding@Home (Shirts & Pande, Science 290, 1903-1904, 2000), where parallel virtual screening processes are executed using donated idle CPU cycles. When benchmarked against the initial vHTS protocol performed on our cluster of 35 nodes, the grid-based protocol finished the same screening with a 2-fold reduction in time performance.

To ensure generality and avoid an exact re-run of the initial screen, different initial conformations and random seeds were assigned to the compounds and the genetic algorithm-based sampling, respectively. The same 80 compounds were present in the top 4% of the ranked database using the grid-based protocol. This is a good indication that sampling of compound conformations, the most variable step of vHTS, was adequate for this work and that our initial ranking was not by chance. Despite a modest 2-fold increase in time at this point, the grid-based vHTS protocol lays a foundation for future large-scale screening and possesses essentially unlimited scalability by utilizing larger number of idle CPUs over the grid network (Richards, Nat. Rev. Drug Discov. 1, 551-555, 2002).

The present teachings include the following aspects.

1. A method of identifying one or more inhibitors of heterodimerization or homodimerization of activated extracellular domains of at least one tyrosine receptor kinase (RTK), the method comprising:
providing, on a digital computer, a molecular model comprising a complex of extracellular dimerization domains of an RTK;
docking a chemical databases to the molecular model;
scoring the compounds comprised by the database; and
identifying one or more high-scoring compounds.

2. A method in accordance with aspect 1, further comprising:
obtaining at least one high-scoring compound;
testing the at least one high-scoring compound for an ability to inhibit tyrosine kinase activity in target cells.

3. A method in accordance with aspect 2, further comprising testing the at least one high-scoring compound for specificity of inhibition of the RTK.

4. A method in accordance with aspect 3, further comprising testing the at least one high-scoring compound for an ability to inhibit chemical cross-linking of the RTK when stimulated with its natural ligand 5. A method in accordance with any one of aspects 1-4, wherein the RTK is EGFR.

6. A novel compound or salt thereof which inhibits dimerization of an RTK, wherein the compound is identified by the method of any one of aspects 1-5.

7. A novel compound or a salt thereof, selected from the group consisting of Compound 11241 or a salt thereof, Compound 309895 or a salt thereof, Compound 303769 or a salt thereof, and Compound 56452 or a salt thereof.

8. A novel compound or a salt thereof, selected from the group consisting of an analog of Compound 11241 or a salt thereof, an analog of Compound 309895 or a salt thereof, an analog of Compound 303769 or a salt thereof, and an analog of Compound 56452 or a salt thereof, wherein the analog or salt thereof is an inhibitor of RTK dimerization.

9. A novel compound or salt thereof of any one of aspects 6-8, wherein the RTK is an EGFR.

10. A method of inhibiting dimerization of an RTK, the method comprising contacting the RTK with a compound or salt thereof of any one of aspects 6-9.

11. A method of inhibiting dimerization of an RTK, the method comprising contacting the RTK with a compound or salt thereof identified by the method of any one of aspects 1-5.

12. A method of inhibiting dimerization of an RTK in accordance with aspect 10 or aspect 11, wherein the RTK is comprised by a cell.

13. A method of treating a disease involving abnormally elevated RTK activity, the method comprising:
selecting an inhibitor of RTK dimerization on the basis of having been identified by the method of any one of aspects 1-5; and
administering a therapeutically effective amount of the inhibitor to a subject in need of treatment.

14. A method of treating a disease involving abnormal RTK activity, the method comprisine, administering a therapeutically effective amount of a compound or salt thereof of any one of aspects 6-9 to a subject in need of treatment.

15. A method of treating a disease in accordance with aspect 13 or aspect 14, wherein the inhibitor is selected from the group consisting of Compound NSC11241, a salt thereof, Compound NSC309895, a salt thereof, Compound NSC303769, a salt thereof, Compound NSC56452 and a salt thereof.

16. A method of treating a disease in accordance with any one of aspects 13-15, wherein the disease comprises a tumor selected from the group consisting of a breast tumor, a prostate tumor, a thyroid tumor, a lung tumor, a hepatoma, a colon tumor, a uterine tumor, an ovarian tumor, a brain tumor and a neuroendocrine tumor.

17. A method of treating a disease in accordance with any one of aspects 13-16, wherein the RTK activity is EGFR activity.

18. A method of treating a disease in accordance with any one of aspects 13-17, further comprising administering an inhibitor of tyrosine kinase activity of the RTK.

All publications, patent applications, patents, and other references mentioned herein are incorporated by reference in their entirety.

What is claimed is:

1. A method of inhibiting dimerization of a receptor tyrosine kinase (RTK), comprising contacting the RTK with a compound represented by the structure:

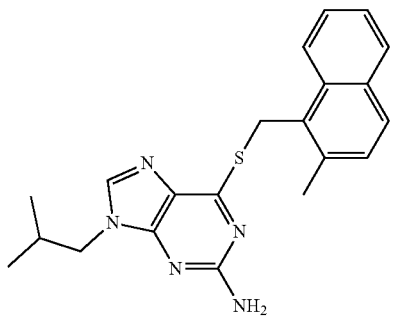 [SMILES: Cc1ccc2ccccc2c1CSc1nc(N)nc2c1ncn2CC(C)C]

or a pharmaceutically acceptable salt thereof.

2. A method of inhibiting dimerization of an RTK in accordance with claim 1, wherein the RTK is an epidermal growth factor receptor (EGFR) kinase.

3. A method of inhibiting dimerization of an RTK in accordance with claim 1, wherein the RTK is comprised by a cell.

4. A method of inhibiting dimerization of an RTK in accordance with claim 3, wherein the cell is a cancer cell.

5. A method of inhibiting dimerization of an RTK in accordance with claim 4, wherein the cancer cell is a cancer cell in vitro.

* * * * *